[US009518948B2](#)

(12) United States Patent
Miyamoto et al.

(10) Patent No.: US 9,518,948 B2
(45) Date of Patent: Dec. 13, 2016

(54) DETECTION DEVICE, POWER RECEPTION DEVICE, POWER TRANSMISSION DEVICE AND NON-CONTACT POWER SUPPLY SYSTEM

(71) Applicant: Sony Corporation, Tokyo (JP)

(72) Inventors: Takashi Miyamoto, Chiba (JP); Hiroaki Nakano, Tokyo (JP); Tomomichi Murakami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 525 days.

(21) Appl. No.: 13/867,235

(22) Filed: Apr. 22, 2013

(65) Prior Publication Data

US 2013/0293026 A1   Nov. 7, 2013

(30) Foreign Application Priority Data

May 7, 2012   (JP) ................. 2012-105768

(51) Int. Cl.
| H01H 31/34 | (2006.01) |
| G01N 27/04 | (2006.01) |
| B60L 11/18 | (2006.01) |
| G01R 33/12 | (2006.01) |
| G01V 3/10 | (2006.01) |
| H01F 38/14 | (2006.01) |
| H02J 7/02 | (2016.01) |

(Continued)

(52) U.S. Cl.
CPC .......... *G01N 27/045* (2013.01); *B60L 11/182* (2013.01); *B60L 11/1833* (2013.01); *G01R 33/123* (2013.01); *G01V 3/10* (2013.01); *H01F 38/14* (2013.01); *H02J 7/025* (2013.01); *B60L 2230/00* (2013.01); *B60L 2270/147* (2013.01); *H02J 5/005* (2013.01); *H02J 2007/0096* (2013.01); *Y02T 10/7005* (2013.01); *Y02T 10/7088* (2013.01); *Y02T 90/121* (2013.01); *Y02T 90/122* (2013.01); *Y02T 90/125* (2013.01); *Y02T 90/14* (2013.01)

(58) Field of Classification Search
USPC .................................... 307/97, 104
See application file for complete search history.

(56) References Cited

U.S. PATENT DOCUMENTS

| 2012/0001493 A1* | 1/2012 | Kudo ............... H02J 5/005 307/104 |
| 2013/0257168 A1* | 10/2013 | Singh .............. H02J 17/00 307/104 |

FOREIGN PATENT DOCUMENTS

| JP | 2007-064930 A | 3/2007 |
| JP | 2012-016125 A | 1/2012 |

(Continued)

OTHER PUBLICATIONS

Japanese Office Action for Japanese Application No. 2012-105768 issued Nov. 10, 2015 with English Translation.

(Continued)

*Primary Examiner* — Danny Nguyen
(74) *Attorney, Agent, or Firm* — Chip Law Group

(57) ABSTRACT

A detection device, including: one or a plurality of magnetic coupling elements configured to have one or a plurality of coils; and a detection unit that measures or calculates an effective resistance values of the magnetic coupling elements or an effective resistance value of a circuit including at least the magnetic coupling elements and determines a presence or absence of a foreign substance based on a change in the effective resistance value.

14 Claims, 10 Drawing Sheets

(51) Int. Cl.
  *H02J 5/00* (2016.01)
  *H02J 7/00* (2006.01)

(56) References Cited

FOREIGN PATENT DOCUMENTS

JP    2013-223258 A    10/2013
WO    2012/047779 A1    4/2012

OTHER PUBLICATIONS

Office Action Received for Japanese Patent Application No. 2012-105768, Mailed on Apr. 5, 2016, 8 Pages of Office Action Including 4 Pages of English Translation.
Neil Kuyvenhoven et al, "Development of a Foreign Object Detection and Analysis Method For Wireless Power Systems", Product Compliance Engineering, 2011 IEEE Symposium on, Oct. 2011, 7 Pages.
Office Action received for Chinese Patent Application No. 201310156684.X, mailed on May 19, 2016, 16 Pages of Office Action including 8 pages of English translation.

\* cited by examiner

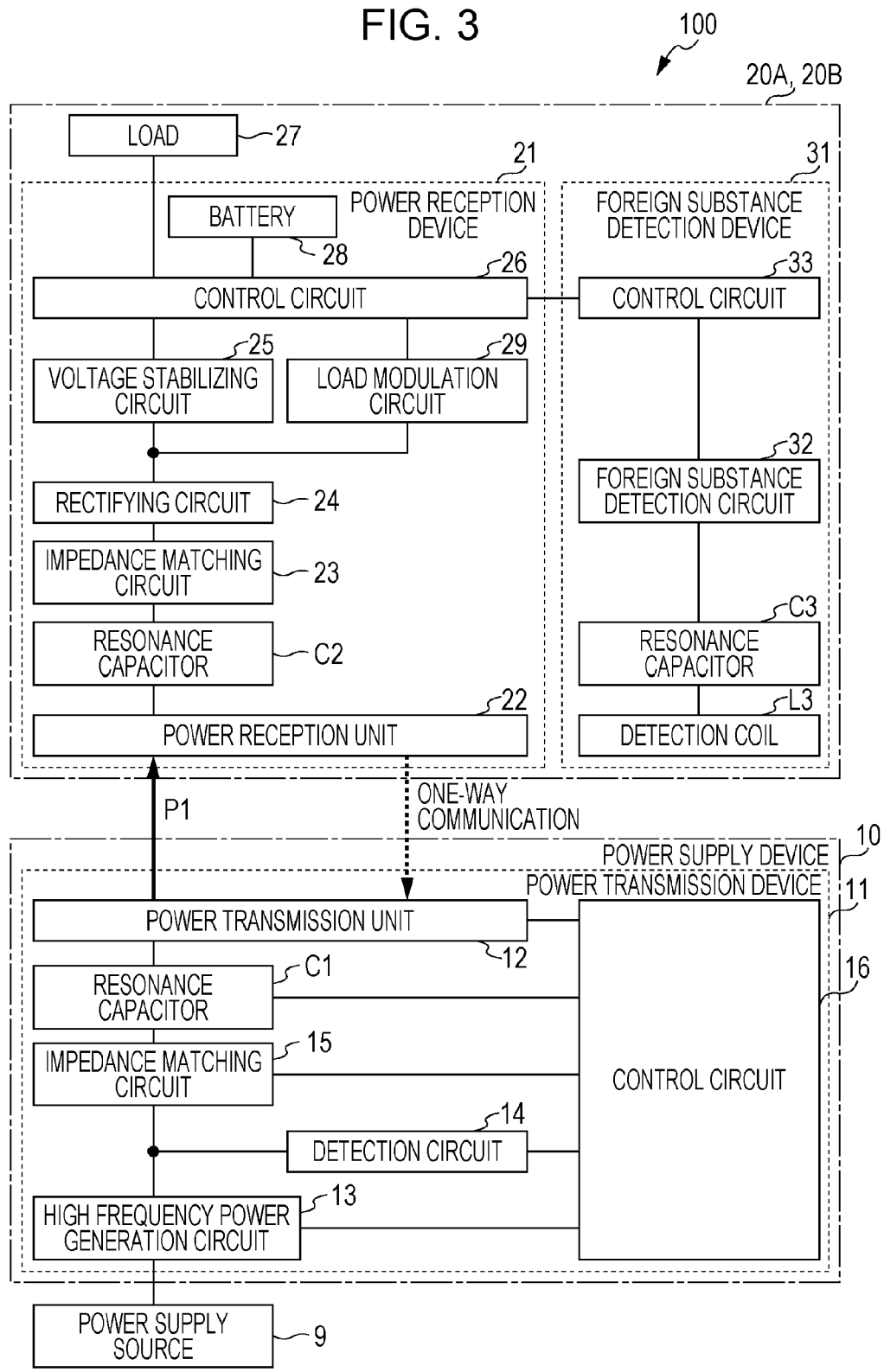

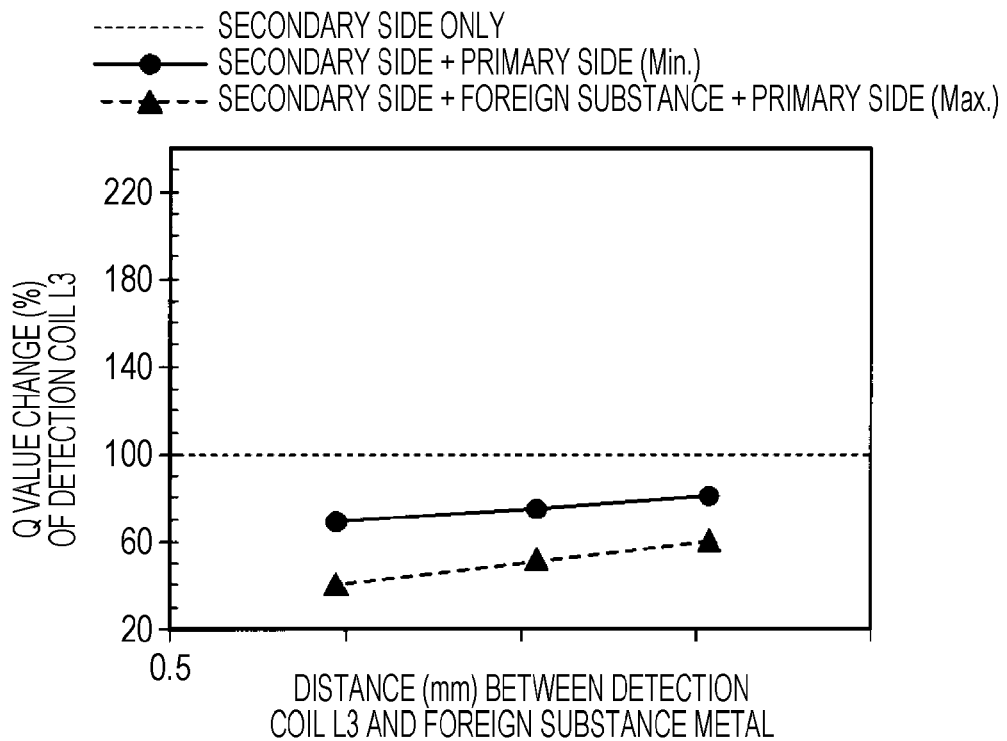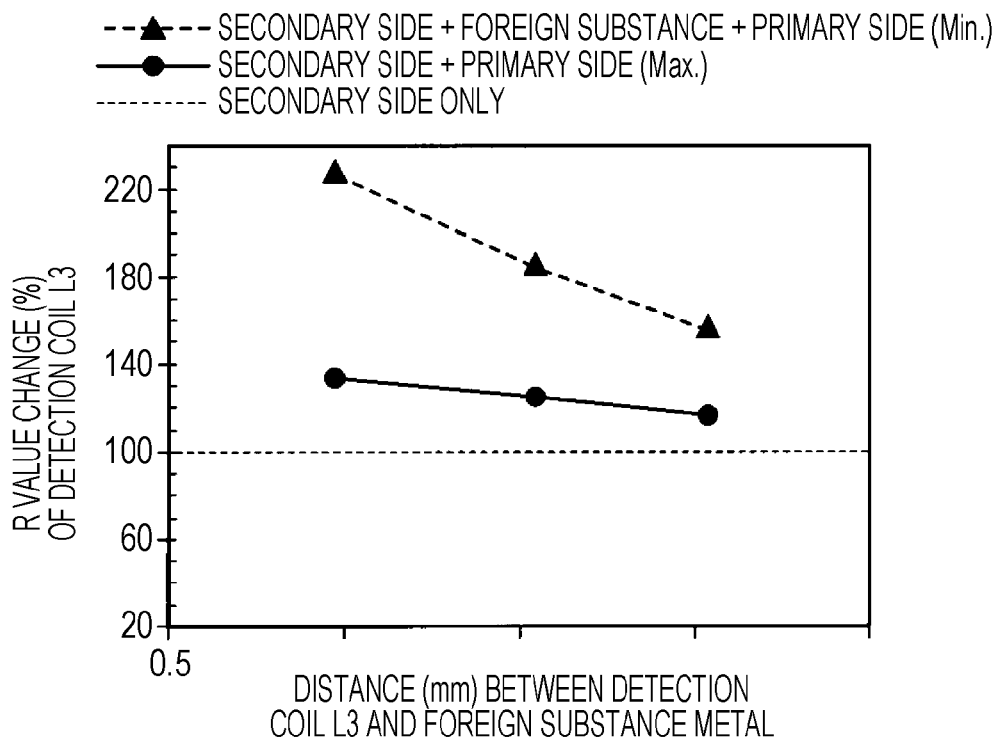

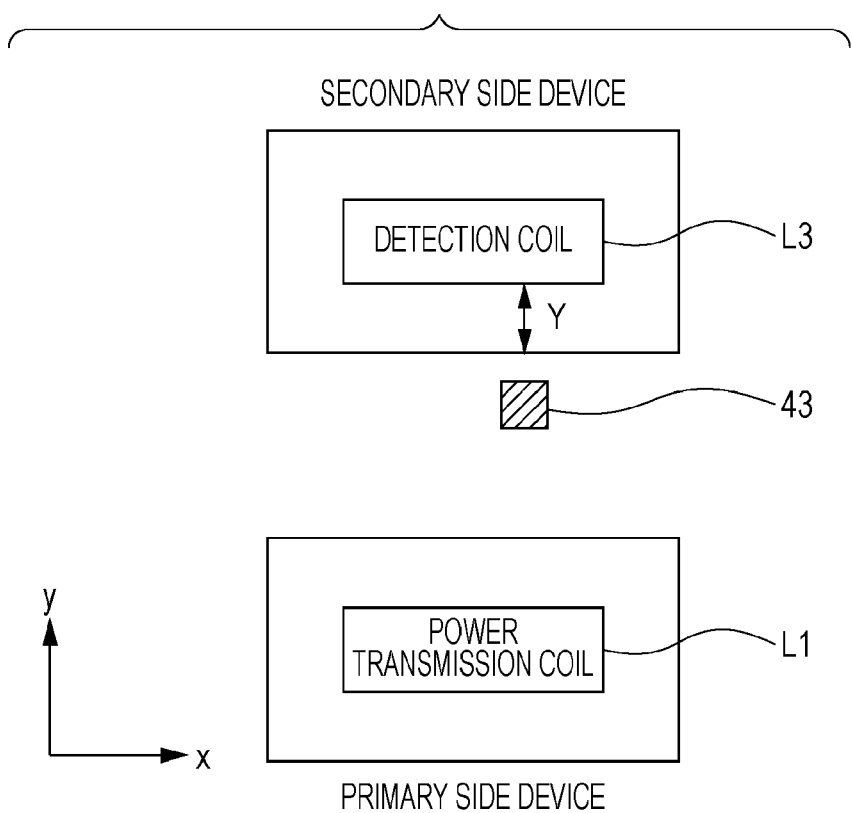

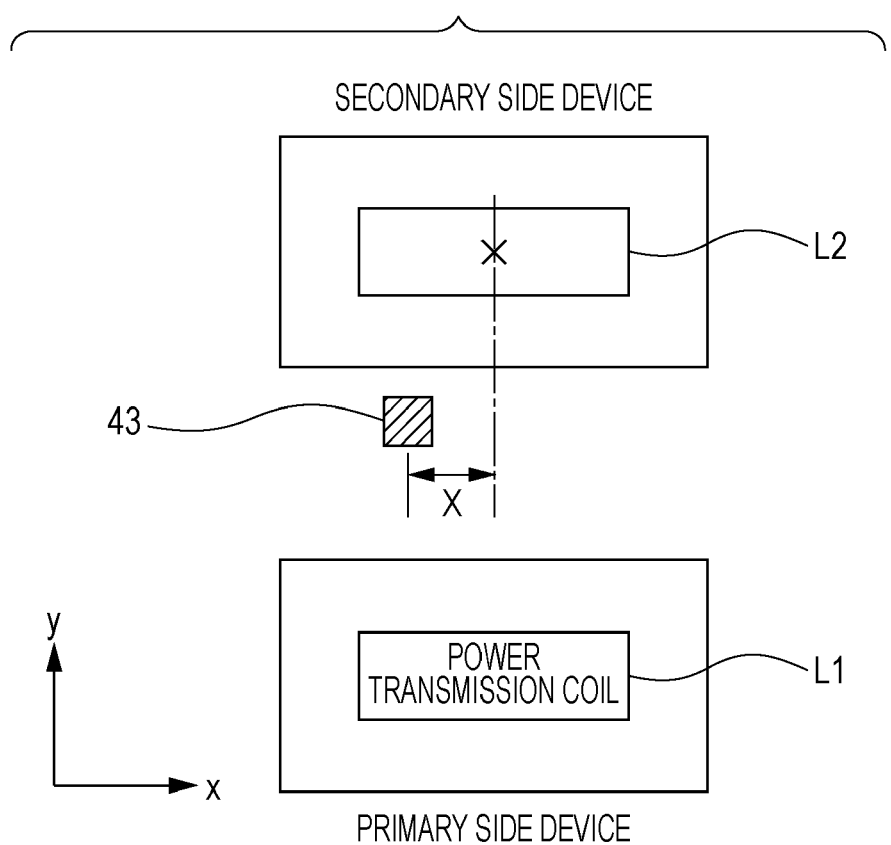

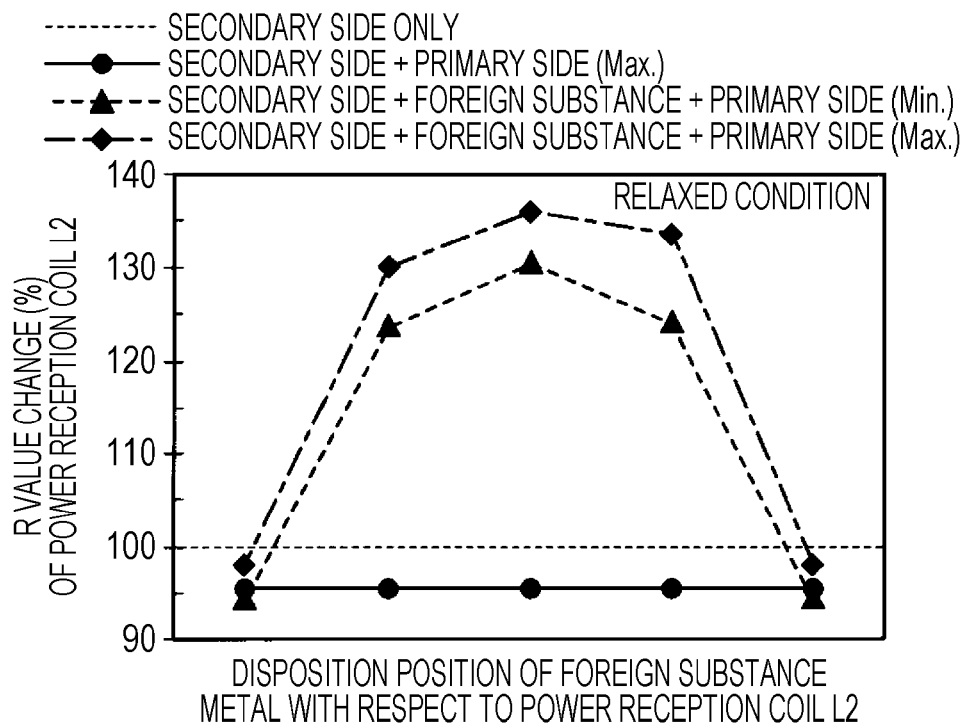
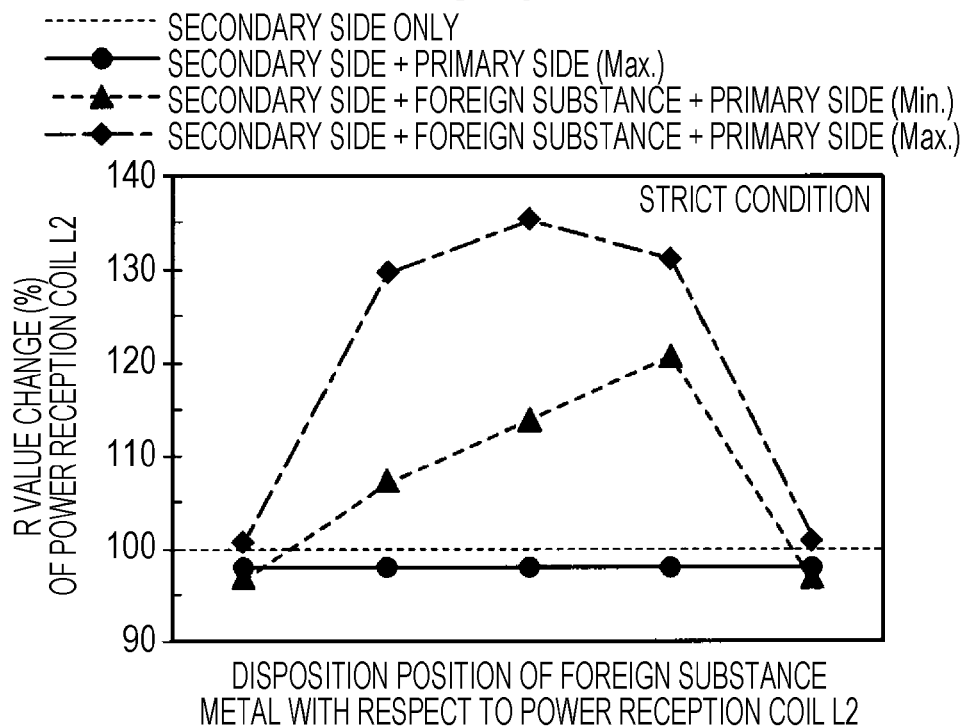

DETECTION DEVICE, POWER RECEPTION DEVICE, POWER TRANSMISSION DEVICE AND NON-CONTACT POWER SUPPLY SYSTEM

BACKGROUND

The present disclosure relates to a magnetic coupling element magnetically coupled to another magnetic coupling element, a foreign substance or the like, a device (magnetic coupling device) and a system (magnetic coupling system) which use the magnetic coupling element.

Particularly, the disclosure relates to a detection device detecting a mixture of the foreign substance (such as a metal, magnetic material, and magnet) heated by a magnetic flux between a non-contact power supply device and an electronic device which configure a non-contact power supply system, a power reception device, a power transmission device and the non-contact power supply system.

In recent years, a power supply system (called as a non-contact power supply system or a non-contact power transmission system) performing the power supply (power transmission) in a non-contact manner with respect to a consumer electronic (CE) device (electronic device for a consumer use) such as a mobile phone and a portable music player, for example has attracted much attention. Accordingly, a power charge can be started by simply putting the electronic device (secondary device) on a charge tray (primary side device) instead of plugging (connecting) a connector of the power supply device such as AC adapter to the CE device. As a result, a terminal connection between the electronic device and the charging tray is not necessary.

In this way, as a method of supplying the power in the non-contact manner, an electromagnetic induction method has been well known. In addition, in recent years, a non-contact power supply system adopting a method which is called a magnetic field resonance method using a resonance phenomenon has attracted attention.

The non-contact power supply system using the magnetic field resonance method has an advantage in that the power can be transmitted between devices which are located further far away from each other compared to the electromagnetic induction method. In addition, even if an alignment between the power supply source (power transmission coil) and a power supply destination (power reception coil) is a little poor, there is an advantage in that transmission efficiency (power supply efficiency) is not lowered too much. However, it is unchanged in that any one of the magnetic field resonance method and the electromagnetic induction method adopts the non-contact power supply system (magnetic coupling system) using the magnetic coupling between the power supply source (power transmission coil; magnetic coupling element) and the power supply destination (power reception coil; magnetic coupling system).

Incidentally, one of the important factors in the non-contact power supply system is a countermeasure against the heat generation of the foreign substance such as a metal, magnetic material, and magnet which generate heat due to the magnetic flux. When supplying the power in the non-contact manner without being limited to the electromagnetic induction method or the magnetic field resonance method, if the foreign substance is mixed in a gap between the power transmission coil and the power reception coil, there is a possibility that the foreign substance may generate heat due to the magnetic flux the foreign substance. In addition, the heat generation of the foreign substance results from a current (eddy current, ring current, circular current) produced in the foreign substance metal by passing through magnetic flux to a magnetic loss (hysteresis loss) occurring in a foreign substance magnetic material or a foreign substance magnet due to the magnetic flus passing through the foreign substance, the foreign substance magnetic material or the foreign substance magnet.

As a countermeasure against the heat generation, there have been proposed many methods which detect the foreign substance by adding a foreign substance detection system to the non-contact power supply system. For example, a method using an optical sensor or a temperature sensor has been known. However, the method using the sensor results in increased costs in a case of a wide power supply range as in the magnetic field resonance method. In addition, for example, according to the temperature sensor, since the output result on the temperature sensor depends on a thermal conductivity around the sensor, the design constraints are also imposed on the devices of a power transmission side and a power reception side.

Therefore, by focusing a change in parameters (current, voltage, and the like) when a foreign substance metal enters between the power transmission side and the power reception side, a method of determining whether or not the foreign substance is present has been proposed. According to such a method, since there is no reason to impose any design constraint or the like, it may be possible to reduce the cost.

For example, Japanese Unexamined Patent Application Publication No. 2008-206231 discloses a method of detecting the foreign substance metal using a modulation degree (change in an amplitude and phase) during a communication between the power transmission side and the power reception side, and Japanese Unexamined Patent Application Publication No. 2001-275280 discloses a method of detecting (foreign substance detection using a DC-DC efficiency) the foreign substance metal using an eddy current loss.

However, the methods proposed in Japanese Unexamined Patent Application Publication Nos. 2008-206231 and 2001-275280 do not take into account an influence due to a metal housing of the power reception side. When considering the power charge to a general-purpose portable device, there is a high possibility that any type of metals (metal housing, metal components, or the like) may be used in the portable device. Therefore, it is difficult to identify a change in parameters resulting from the "influence due to the metal housing", or otherwise from "mixing of the foreign substance metal". If Japanese Unexamined Patent Application Publication No 2001-275280 exemplified as one example, it is not possible to identify whether the eddy current loss occurs in the metal housing or otherwise occurs due to the foreign substance metal mixed between the power transmission side and the power reception side. In this way, it is to be understood that the techniques proposed in Japanese Unexamined Patent Application Publication Nos. 2008-206231 and 2001-275280 are unable to accurately detect the foreign substance metal.

SUMMARY

It is desirable to improve detection accuracy by detecting a foreign substance present in the vicinity of a detection coil, that is, a magnetic coupling element without providing a new sensor.

According to an embodiment of the present disclosure, there is provided a detection device including: one or a plurality of magnetic coupling elements configured to have one or a plurality of coils; and a detection unit that measures or calculates an effective resistance values of the magnetic coupling elements or an effective resistance value of a circuit including at least the magnetic coupling elements and determines a presence or absence of a foreign substance based on a change in the effective resistance value.

In a case where the magnetic coupling element and the foreign substance metal are magnetically coupled, a Q value of the magnetic coupling element (resonance circuit) is lowered, due to two reasons that the effective resistance value of the magnetic coupling element is increased and an inductance value of the magnetic coupling element is decreased. Therefore, in a case where the inductance value of the magnetic coupling element is significantly changed due to some kind of factors, focusing on the effective resistance value of the magnetic coupling element (resonance circuit) enables a higher detection accuracy of the foreign substance metal rather than focusing on the Q value of the magnetic coupling element (resonance circuit).

According to at least an embodiment of the present disclosure, the foreign substance present in the vicinity of the magnetic coupling element may be detected without providing a new sensor and the detection accuracy may be improved.

BRIEF DESCRIPTION OF THE DRAWINGS

FIG. 3 is a block diagram illustrating a configuration example of the non-contact power supply system according to the embodiment of the present disclosure;

FIGS. 5A and 5B are views illustrating one example of a measurement result related to a change in electric properties (Q value, R value) of a detection coil due to presence or absence of a foreign substance metal;

FIG. 6 is a view illustrating a distance adjustment between the detection coil and the foreign substance metal;

FIG. 8 is a view illustrating adjustment of a disposition position of the foreign substance metal with respect to the power reception coil;

FIGS. 9A and 9B are views illustrating one example of the measurement result related to a change in the R value of a power reception coil due to presence or absence of a foreign substance metal;

DETAILED DESCRIPTION OF EMBODIMENTS

Figure 1:
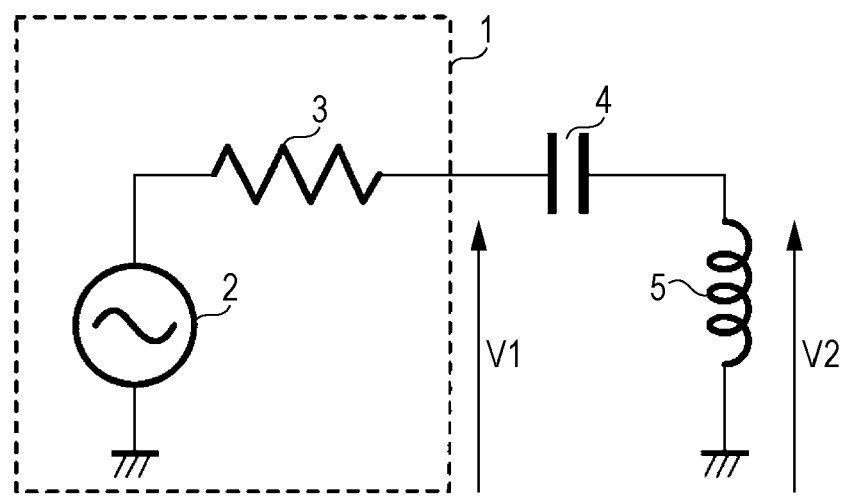
FIG. 1 is a schematic circuit diagram illustrating a Q value measurement used as one example of a foreign substance metal detection in the present disclosure.

Hereinafter, an example for embodying the present disclosure (hereinafter, referred to as an embodiment) will be described.

The description will be made in the following order. In addition, in the specification and drawings, component elements having substantially the same functions and configurations will be denoted with the same reference numerals and the description thereof will not be repeated.

1. Introduction Description
2. Q Value Measurement Principle
3. R Value Measurement Principle
4. Description on Non-Contact Power Supply System
5. Measurement Data (1)
6. Measurement Data (2)
7. Modification Example
8. Others 1. Introduction Description In the present disclosure, there is proposed a magnetic coupling system in which a foreign substance metal detection is performed based on an effective resistance value of a magnetic coupling element (high frequency resistance value, Rs value, R value) of a power transmission side or a power reception side, or an effective resistance value of a circuit including at least the magnetic coupling element, when performing a power charge to a battery of the power reception side (secondary side) and the like by supplying a power from the power transmission side (first side). The magnetic coupling system according to an embodiment of the present disclosure measures or calculates the effective resistance value of one or a plurality of magnetic coupling elements magnetically coupled outward or the effective resistance value of the circuit including at least one or a plurality of the magnetic coupling elements, in the power transmission side or the power reception side. Then, based on a measurement result or calculation result on the effective resistance value, presence or absence of a foreign substance in the vicinity of the magnetic coupling element is determined.

However, in a case of using the same measurement principle as in a measurement device such as an LCR meter or an impedance analyzer, it is difficult to accurately measure the effective resistance value, a Q value (Quality factor) or the like of a resonance circuit in a frequency in the vicinity of the resonance frequency of the resonance circuit. These measurement devices enables applying a predetermined high frequency electric power to the magnetic coupling element, measuring an amplitude and phase of a voltage and current which are generated during that time, and calculating the effective resistance value or the Q value of the magnetic coupling element. However, the amplitude and phase of the voltage and current are rapidly changed due to the frequency change in the high frequency electric power. Accordingly, it may not be possible to obtain sufficient measurement accuracy. Thus, an example will be described in which the Q value of the resonance circuit is measured using a voltage ratio of the resonance circuit (amplitude ratio), a half value width method or the like and then the effective resistance value is calculated (estimated) using the measurement result. The Q value is an index indicating a relationship between a retention and loss of energy and is generally used as a value indicating a sharpness of a resonance peak (strength of the resonance) of the resonance circuit.

In addition, in the description according to each embodiment of the present disclosure, the detection of the foreign substance metal will be described as an example, but the detection of other foreign substance (foreign substance magnetic material, foreign substance magnet, and the like) is also the same.

2. Q Value Measurement Principle

Hereinafter, the Q value principle will be described with respect to the drawings.

FIG. 1 is a schematic circuit diagram illustrating the Q value measurement used when detecting the foreign substance metal according to the present disclosure.

The circuit illustrated in FIG. 1 is an example of a basic circuit configuration (case of magnetic coupling) indicating the Q value measurement principle and for example, is provided with a signal source 1 including an AC power source 2 generating an AC signal (sine wave) and a resistance element 3, a capacitor (referred to as a condenser) 4 and a coil 5. The resistance element 3 illustrates an internal resistor (output impedance) of the AC power source 2. The capacitor 4 and the coil 5 are connected to form a series resonance circuit (an example of the resonance circuit) with respect to the signal source 1. Then, the resonance circuit performs the resonance with a predetermined resonance frequency (fr) by capacitance values (C value and C) of the capacitor 4 and inductance values (L value and L) of the coil 5.

Here, if a voltage (amplitude) between both ends of the coil 5 and the capacitor 4 which configure the series resonance circuit is assumed as V1 (an example of the voltage applied to the resonance circuit) and the voltage (amplitude) between both ends of the coil 5 is assumed as a V2, the Q value of the series resonance circuit is represented by the formula (1), in the frequency of the AC signal of the AC power source 2. In addition, when voltage V2>>voltage V1, the formula may be approximately represented.

$$Q = \frac{V2 - V1}{V1} \cong \frac{V2}{V1} \quad (1)$$

For example, in the circuit illustrated FIG. 1, the voltage V1 is multiplied by Q times to obtain the voltage V2. In addition, in a case where the AC signal frequency of the AC power source 2 is changed, the frequency in which the voltage ratio (V2/V1) of the voltage V2 to the voltage V1 becomes the maximum becomes the resonance frequency (fr) of the LC resonance circuit configured to have the coil 5 and the resonance capacitor 4. In this manner, focusing on a voltage ratio (V2/V1) of the voltage V2 to the voltage V1, it may be possible to measure, with a high accuracy, the resonance frequency (fr) of the resonance circuit and the Q value (Q) of the resonance circuit in the resonance frequency.

Further, even with the half value width method of obtaining the Q value of the resonance circuit from the half value width of the sharpness (strength of the resonance) of the resonance peak of the resonance circuit, it may be possible to measure, with a high accuracy, the resonance frequency (fr) of the resonance circuit and the Q value (Q) of the resonance circuit in the resonance frequency. In this case, a frequency in which a frequency property related to the impedance (Z) or admittance (Y) of the resonance circuit is at a peak becomes the resonance frequency.

3. R Value Measurement Principle

Incidentally, if there is for example, a metal piece as a foreign substance metal in the vicinity of the coil 5, magnetic force lines pass through the metal piece and thereby the eddy current is generated. As for the coil 5, since the metal piece and the coil 5 are magnetically coupled and a resistance load is seemingly applied to the coil 5, the R value (effective resistance value, R) of the magnetic coupling element is increased and the Q value (Q) of the magnetic coupling element (resonance circuit) is lowered. Further, since the metal piece and the coil 5 are magnetically coupled, the L value (L) of the magnetic coupling element is decreased and the Q value (Q) of the magnetic coupling element (resonance circuit) is lowered in the same manner.

That is, in a case where the magnetic coupling element and the foreign substance metal are magnetically coupled, the Q value (Q) of the magnetic coupling element (resonance circuit) is lowered because of two reasons that the R value (R) of the magnetic coupling element is increased and the L value (L) of the magnetic coupling element is lowered. This is also apparent from the formula (2). In addition, in a case where the AC signal frequency of the AC power 2 is approximately the same as the resonance frequency (fr) of the resonance circuit, it may be possible to represent the Q value of the resonance circuit by the formula (2). However, R is an effective resistance value of the resonance circuit in the resonance frequency (fr), L is an inductance value of the coil 5 in the resonance frequency (fr), and C is a capacitance value of the resonance capacitor 4 in the resonance frequency (fr).

$$Q = \frac{1}{R}\sqrt{\frac{L}{C}} = 2\pi f_r \frac{L}{R} \quad (2)$$

Therefore, in a case where the L value is changed significantly due to some factors, focusing on the R value magnetic coupling element (resonance circuit) has a higher foreign substance metal detection accuracy than focusing on the Q value of the magnetic coupling element (resonance circuit). In addition, since there is an extremely close relationship between an increasing amount of the R value of the magnetic coupling element (resonance circuit) in the case where the magnetic coupling element is magnetically coupled to the foreign substance metal and the heat generation degree of the foreign substance metal, it is very advantageous to have the foreign substance detection system which focuses on the increasing amount of the R value of the magnetic coupling element (resonance circuit).

However, as described above, it is difficult to measure the effective resistance value in the frequency in the vicinity of the resonance frequency of the resonance circuit using the same principle as in the measurement device such as the LCR meter or the impedance analyzer. Accordingly, a technique is proposed in which the Q value of the resonance circuit is measured using the voltage ratio of the resonance circuit or the half width method or the like and then the R value is calculated (estimated) from the measurement result thereof.

$$R = 2\pi f_r \frac{L}{Q} = \frac{1}{2\pi f_r C Q} \quad (3)$$

$$f_r = \frac{1}{2\pi\sqrt{LC}} \quad (4)$$

$$L = \frac{1}{4\pi^2 f_r^2 C} \quad (5)$$

Here, the R value (R) of the resonance circuit can be represented by the formula (3). This is because the resonance frequency (fr) of the resonance circuit can be represented by formula (4), and the L value (L) of the magnetic coupling element (resonance circuit) can be represented by formula (5). The L represented by the formula (5) is substituted for the L of the formula (3). By the formula (3), the R value (R) of the resonance circuit at the resonance frequency can be calculated, if three values of the C value (C) of the capacitor configuring the resonance circuit, the resonance frequency (fr) of the resonance circuit, and the Q value (Q) of the magnetic coupling element (resonance circuit) are known. However, the C value of the capacitor is considered as the almost known value. Therefore, the R value of the resonance circuit can be calculated (estimated), if two values of the resonance frequency of the resonance circuit and the Q value of the resonance circuit are substantially known. That is, if the two values of the resonance frequency of the resonance circuit and the Q value of the resonance circuit are measured using the voltage ratio of the resonance circuit described above, the half value width method or the like, the R value in the resonance frequency of the resonance circuit can be calculated (estimated).

As described above, if the metal piece is present in the vicinity of the coil 5, the R value of the magnetic coupling element (resonance circuit) is increased due to the influence of the eddy current generated in the metal piece and thereby the metal piece generates heat due to the eddy current. Therefore, if the change (increase) in the R value is detected, the metal piece present in the vicinity of the coil 5 can be detected. In other words, the R value measurement as described above can be adapted to the detection of the foreign substance metal inserted between the power transmission side (primary side) and the power reception side (secondary side).

Then, by performing the process of detecting the foreign substance metal with focusing on the change in the R value as described above, the foreign substance metal can be detected with a high accuracy without resort to the electromagnetic induction method or the magnetic field resonance method. Therefore, it may be possible that the user removes the foreign substance metal therefrom.

In addition, in a frequency which is remarkably different from the resonance frequency of the resonance circuit, the R value of the resonance circuit can be measured with a high accuracy using the same measuring principle as the measurement device such as the LCR meter and the impedance analyzer. However, in this case, for convenience, the R value of the resonance circuit is measured in the frequency which is remarkably different from the resonance frequency of the resonance circuit. As a result, since the change in the R value of the resonance circuit due to presence or absence of the metal foreign substance is reduced, there is a high possibility that the detection accuracy of the foreign substance metal may be lowered.

On the other hand, in a case where the R value of the coil 5 is directly measured by electrically separating the resonance capacitor 4 and the coil 5 which configure the resonance circuit using switches and the like, it may be possible to measure the R value of the coil 5 with a high accuracy, using the same measurement principle as the measurement device such as the LCR meter, the impedance analyzer or the like, even in the frequency substantially the same as the resonance frequency of the resonance circuit. That is, if there is provided the foreign substance detection system which changes the configuration of the resonance circuit by way of switching only a time period for detecting the foreign substance, even in the frequency substantially the same as the resonance frequency of the resonance circuit, it may be possible to detect the presence or absence of a foreign substance metal, using the same measurement principle such as the LCR meter, the impedance analyzer or the like. However, in such a case, there are many problems to be solved, such as the resistance value of the switching portion, the loss due to the switching.

As described above, there are many techniques to measure (calculate, estimate) the R value of the magnetic coupling element (resonance circuit). In the foreign substance detection system proposed in the present specification, in order to measure (calculate, estimate) the R value of the magnetic coupling element (resonance circuit) using some type of means, presence or absence of a foreign substance metal may be determined using the change in the R value.

4. Description on Non-Contact Power Supply System

Next, the non-contact power supply system to which a technique of the present disclosure is adopted will be described.

Entire Configuration of Non-Contact Power Supply System

Figure 2:
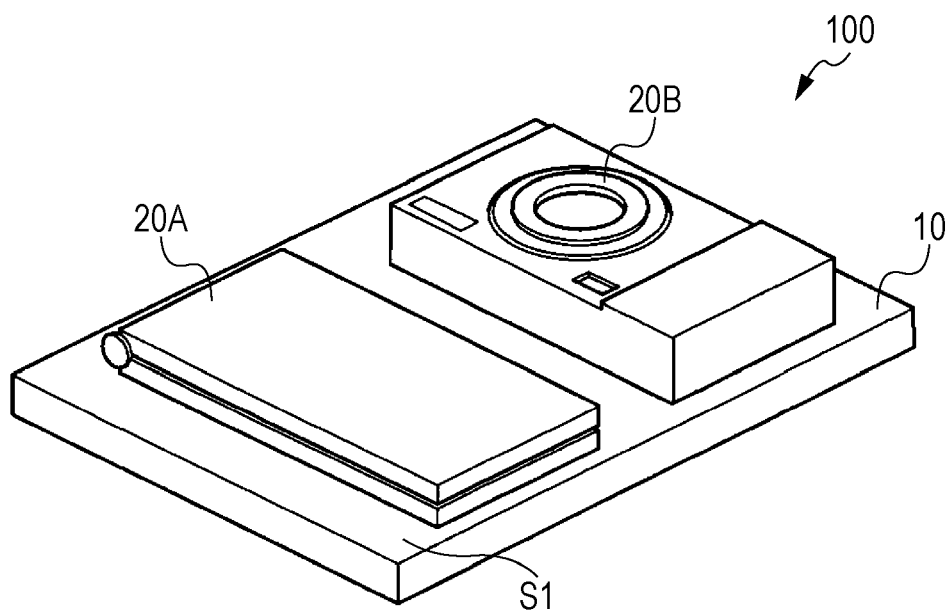
FIG. 2 is a schematic outline view of a non-contact power supply system according to one embodiment of the present disclosure.

FIG. 2 illustrates a schematic configuration example of the non-contact power supply system according to one embodiment of the present disclosure, and FIG. 3 illustrates a block configuration example of the non-contact power supply system according to one embodiment of the present disclosure.

The non-contact power supply system 100 illustrated in FIG. 2 is a system of performing the power transmission (power supply) in a non-contact manner using the magnetic field (using the magnetic field resonance method in the present embodiment). The non-contact power supply system 100 is provided with a power supply device 10 (primary side device) or an electronic device (secondary side device) as one or a plurality of the power supply target devices. Here, the power supply target device is provided with for example, electronic devices 20A to which a mobile phone terminal device and 20B to which an electronic still camera is applied, for example, as the power supply target device. The power supply target device is not limited thereto and may be an electronic device capable of receiving the power in the non-contact manner from the power supply device 10.

The non-contact power supply system 100 has for example, the configuration as illustrated in FIG. 2, in which the electronic devices 20A and 20B are positioned on or move close to a power supply surface (power transmission surface) S1 in the power supply device 10 so that the power transmission can be performed with respect to the electronic devices 20A and 20B from the power supply device 10. Here, considering the case where the power transmission is performed at the same time or in a time sharing manner (sequentially) with respect to the a plurality of electronic devices 20A and 20B, the power supply device 10 has a power supply surface S1 in a larger mat shape (or tray shape) than the area of the power supply target electronic devices 20A and 20B.

Configuration Example of Power Supply Device

As described above, the power supply device 10 is that (for example, charging tray) for performing the power transmission with respect to the electronic devices 20A and 20B, using the magnetic field. The power supply device 10, for example, as illustrated in FIG. 3, is provided with a power transmission device 11 for performing the power transmission, using the power supplied from an external power supply source 9 of the power supply device 10. The external power supply source 9 is a commercial power source supplied via a so-called electrical outlet, a plug socket as an example.

The power transmission device 11 is configured to have, for example, a power transmission unit 12, a high frequency power generation circuit 13, a detection circuit 14, an impedance matching circuit 15, a control circuit 16 and a capacitor C1 (capacitance element). The power transmission device 11 in this example is provided with the detection circuit 14 and the control circuit 16, and thereby is a block configuration which enables the non-contact power supply system 100 to perform a one-way communication using a load modulation. However, when considering the one-way communication or a two-way communication by means other than the load modulation, the configuration is not limited thereto.

The power transmission unit 12 is configured to include a power transmission coil (primary side coil) L1 and the like to be described later. The power transmission unit 12 performs the power transmission which utilizes performed by means of the magnetic field with respect to the electronic devices 20A and 20B (specifically, a power reception unit 22 to be described later), using the power transmission coil L1 and the resonance capacitor C1. Specifically, the power transmission unit 12 has a function of radiating the magnetic field (magnetic flux) toward the electronic devices 20A and 20B from the power supply surface S1.

The high frequency power generation circuit 13 is a circuit for generating a predetermined high frequency power (AC signal) for performing the power transmission to perform the power transmission, using the power supplied from the external power supply source 9 of the power supply device 10, for example.

The detection circuit 14 has a function of detecting (demodulating) a modulation signal using a load modulation circuit 29 to be described later and is a circuit for supplying a detection result to the control circuit 16.

The impedance matching circuit 15 is a circuit for performing an impedance match when performing the power transmission. This allows an efficiency (transmission efficiency) to be improved during the power transmission. In addition, depending on the configurations of the power transmission coil L1, a power reception coil L2 to be described later or resonance capacitors C1 and C2, the impedance matching circuit 15 may not be provided. Further, if there is no problem with the lowered transmission efficiency, this impedance matching circuit 15 may not be provided.

The resonance capacitor C1 is a capacitance element for configuring both an LC resonance device (resonance circuit) and the power transmission coil L1 of the power transmission unit 12, and is disposed to be electrically connected to the power transmission coil L1 in series, parallel or a combination of series and parallel. The LC resonance device configured to have the power transmission coil L1 and the resonance capacitor C1 is able to perform the resonance operation using the resonance frequency f1 (first resonance frequency) formed from a frequency substantially the same as or in the vicinity of the high frequency power generated in the high frequency power generation circuit 13. In addition, the capacitance value of the resonance capacitor C1 is set to be such a resonance frequency f1.

However, if the above resonance frequency f1 can be realized through the resonance operation using a parasitic capacitance component (floating capacitance component) configured from the capacitance between lines in the power transmission coil L1 and the capacitance between the power transmission coil L1 and the power reception coil L2 to be described later, the resonance capacitor C1 may not be provided. In addition, if there is no problem with the lowered transmission efficiency, similarly, the resonance capacitor C1 may not be provided.

The control circuit 16 is a circuit for receiving the detection result on the detection circuit 14 and for controlling the high frequency power generation circuit 13, the impedance matching circuit 15, the resonance capacitor C1, the power transmission unit 12 or the like.

For example, a case is assumed whether or not the foreign substance metal presents between the power transmission unit 12 and the power reception unit 22 is detected by a foreign substance detection device 31 (to be described later) in the electronic devices 20A and 20B. At this time, the load modulation is performed in a load modulation circuit 29 (to be described later similarly) in the electronic devices 20A and 20B to change the detection result on the detection circuit 14. Therefore, it may be possible to recognize the present of the foreign substance metal using the control circuit 16 of the power transmission device 11 side and to limit or to stop the power transmission using the control of the control circuit 16. On the other hand, the control circuit 16 receives the detection result on the detection circuit 14 and performs a pulse width modulation control (PWM control) of the high frequency power generation circuit 13 or a switching control of the impedance matching circuit 15, the resonance capacitor C1, the power transmission unit 12 and the like. It may also be possible to perform an automatic control to maintain the high transmission efficiency (power supply efficiency) using such a control of the control circuit 16.

Configuration Example of Electronic Device

The electronic devices 20A and 20B adopt stationary type electronic devices represented by the television receivers, for example or portable type electronic devices including a charging cell (battery) represented by mobile phones or digital cameras. The electronic devices 20A and 20B have the same function with respect to the power supply, and therefore herein, the electronic device 20A will be described as a representative as.

For example, as illustrated in FIG. 3, the electronic device 20A is provided with the power reception device 21 and a load 27 performing a predetermined operation (operation exhibiting a function as the electronic device) based on the power supplied from the power reception device 21. In addition, the electronic device 20A is also provided with a foreign substance detection device 31 to detect presence or absence of a foreign substance metal between (in a gap) the power transmission unit 12 and the power reception unit 22.

Hereinafter, the power reception device 21 will be described.

The power reception device 21 has for example, a power reception unit 22, a resonance capacitor (capacitance element) C2, an impedance matching circuit 23, a rectifying circuit 24, a voltage stabilizing circuit 25, a control circuit 26 and a battery 28. The power reception device 21 in this example is provided with a load modulation circuit 29 and the control circuit 26, and thereby configures a block configuration which enables the non-contact power supply system 100 to perform the one-way communication using the load modulation. However, when considering the one-way communication or two-way communication using means except for the load modulation, the configuration is not limited thereto.

The power reception unit 22 is configured to include a power reception coil (secondary coil) L2 to be described later. The power reception unit 22 has a function of receiving the power transmitted from the power transmission unit 12 in the power supply device 10 using the power reception coil L2 and the resonance capacitor C2.

The resonance capacitor C2 is a capacitance element for configuring the LC resonance device (resonance circuit) together with the power reception coil L2 of the power reception unit 22, and is disposed to be electrically connected to the power reception coil L2 in series, parallel or in combination of the series and parallel. The LC resonance device configured to have the power reception coil L2 and the resonance capacitor C2 causes the resonance operation to be performed using the resonance frequency f2 formed from the frequency substantially the same as or in the vicinity of the high frequency power generated in the high frequency power generation circuit 13 of the power transmission device 11. That is, the LC resonance device in the power transmission device 11 formed from the power transmission coil L1 and the resonance capacitor C1, and the LC resonance device in the power reception device 21 formed from the power reception coil L2 and the resonance capacitor C2 are caused to perform the resonance operation using the resonance frequencies (f1≈f2) approximately equal to each other. In addition, the capacitance value of the resonance capacitor C2 is set to be such resonance frequency f2.

However, if the resonance frequency f2 is realized by the resonance operation using the parasitic capacitance component configured to have the capacitance between lines in the power reception coil L2 and the capacitance between the power transmission coil L1 and the power reception coil L2, the resonance capacitor C2 may not be also provided. In addition, if there is no problem of the lowered transmission efficiency, the resonance frequencies f1 and f2 may be different from each other (f2≠f1) or the resonance capacitor C2 may not be provided.

The impedance matching circuit 23 is a circuit for performing impedance matching when performing the power transmission similarly to the impedance matching circuit 15 of the power transmission device 11 described above. In addition, depending on the configurations of the power transmission coil L1, or the power reception coil L2 to be described later, the resonance capacitors C1 and C2, the impedance matching circuit 23 may not be provided. Further, if there is no problem of the lowered transmission efficiency, similarly this impedance matching circuit 23 may not be provided.

The rectifying circuit 24 is a circuit to rectify the power (AC power) supplied from the power reception unit 22 and to generate the DC power. In addition, there are many cases where a smooth circuit (not illustrated) for smoothing the power after being rectified is provided between the rectifying circuit 24 and a voltage stabilizing circuit 25 to be described later.

The voltage stabilizing circuit 25 is a circuit for performing a predetermined voltage stabilizing operation based on the DC power supplied from the rectifying circuit 24 and for performing the charging with respect to the battery 28 or the battery (not illustrated) in the load 27.

The battery 28 is to reserve the power in response to the charging by the voltage stabilizing circuit 25 and configured using a charging battery (secondary battery) such as for example, a lithium battery and the like. In addition, in a case where only the battery in the load 27 is used, the battery 28 may not be necessarily provided.

The load modulation circuit 29 is a circuit for modulating the load and the change in the power state resulted from the load modulation can be detected by the detection circuit 14 in the power transmission device 11. That is, if the load modulation circuit 29 or the control circuit 26 is provided, even though a special communication apparatus is not provided in the electronic device 20A, it may be possible to transmit the information of the power reception device 21 side to the power transmission device 11 side.

The control circuit 26 is a circuit for performing the control of the power charging operation with respect to the battery 28 or the battery (not illustrated) in the load 27. Moreover, the control circuit 26 is a circuit for controlling the load modulation in the load modulation circuit 29 and controls the power transmission device 11 side to be able to recognize that the foreign substance metal has been detected in such a manner that a change in the power state due to the load modulation is detected by the detection circuit 14 inside the power transmission device 11. In addition, in the control circuit 26, in a case where the foreign substance detection device 31 (to be described later) inside the electronic device 20A detects that the foreign substance metal is present between the power transmission unit 12 and the power reception unit 22, it may be possible to limit or stop the power transmission to the power reception device 21 inside the electronic device 20A by performing the charging control.

Hereinafter, the foreign substance detection device 31 will be described.

The foreign substance detection device 31 has for example, a detection coil L3, a resonance capacitor C3, a foreign substance detection circuit 32 and a control circuit 33. As an example, the detection unit is configured to have the foreign substance detection circuit 32 and the control circuit 33.

The detection coil L3 is an example of the magnetic coupling element separately provided from the power transmission coil L1 and the power reception coil L2, which detects the foreign substance metal.

The resonance capacitor C3 is the capacitor (refer to FIG. 4A) connected to the detection coil L3 so as to be electrically configured in series or is the capacitors (resonance capacitors C3-1 and C3-2) (referred to FIGS. 4B and 4C) connected to the detection coil L3 so as to be electrically configured in a combination of series and parallel. By connecting the detection coil L3 to the resonance capacitor C3, the detection coil L3 performs the resonance (LC resonance) at a predetermined frequency f3.

Further, in a case where the Q value of the LC resonance device (resonance circuit) is calculated from the voltage ratio as will be described later, at least any one of the resonance capacitor C3 has to be connected to the detection coil L3 in series (refer to FIGS. 4A, 4B and 4C). However, in a case where the Q value of the LC resonance device is calculated by other means such as the half value width except for the voltage ratio, the resonance capacitor C3 may be connected with a configuration (not illustrated) electrically connected in parallel with respect to the detection coil L3.

The foreign substance detection circuit 32 is a circuit for measuring the Q value of the detection coil L3, or the Q value of the LC resonance device configured to have the detection coil L3 and the resonance capacitor C3. In addition, there is also a case where it is desirable to measure the Q value using the AC signal frequency (f3; f3≠f1, f3≠f2) which is different from the AC signal frequency (f1, f2; f1≈f2) flowing to the power transmission coil L1 and the power reception coil L2 so as to reduce the unnecessary noise generated in the detection coil L3, but the case is not limited thereto.

Figure 4A:
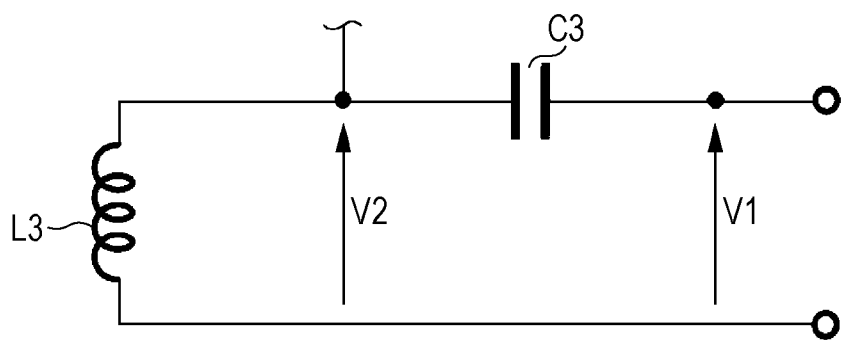
FIGS. 4A to 4C are circuit diagrams illustrating configuration examples of a resonance circuit.
Figure 4B:
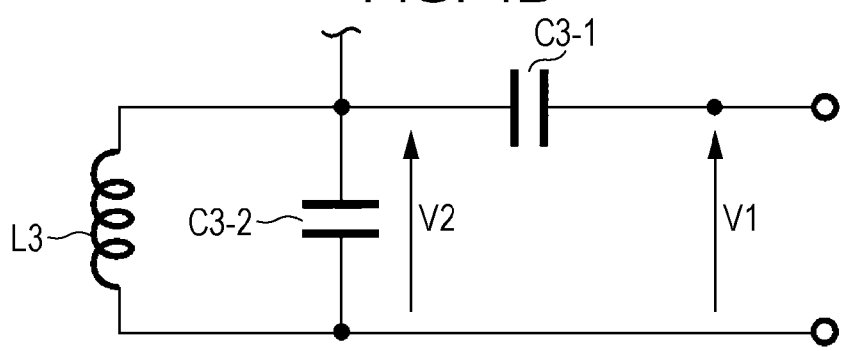
Figure 4C:
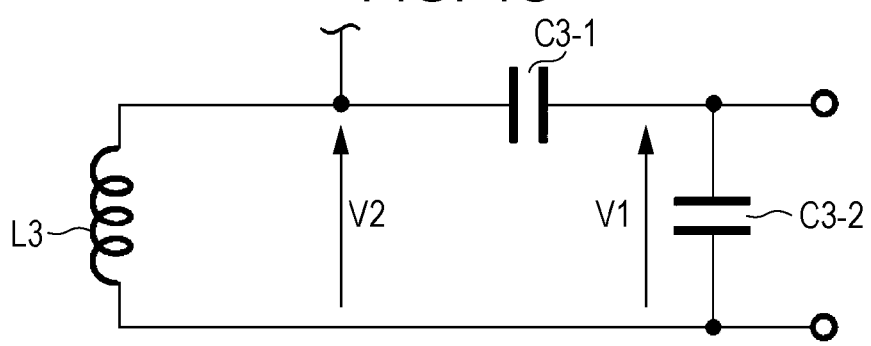

The Q value of the detection coil L3 or the Q value of the LC resonance device configured to have the detection coil L3 and the resonance capacitor C3 is measured, for example, by measuring voltage values at two locations (voltage value V1 and voltage value V2) illustrated FIGS. 4A, 4B and 4C as described above using the foreign substance detection circuit 32, and thereby can be calculated from the ratio (V2V1).

In addition, if the frequency characteristics related to the impedance, the admittance and the like can be measured by the foreign substance detection circuit 32, the Q value of the detection coil L3 or the LC resonance device can also be calculated from the ratio (peak frequency/half value width) of the peak frequency in which the frequency characteristics are at the a peak and a frequency width (half value width) in which the peak value is halved.

In addition, the Q value can be calculated from the ratio of a real part component and an imaginary part component of the impedance of the resonance circuit. The real part component and the imaginary part component of the impedance can be obtained using an auto balancing bridge circuit and a vector ratio detector, for example.

Then, the foreign substance detection circuit 32 obtains by calculating the effective resistance value (R value) in the resonance frequency of the magnetic coupling element or the resonance circuit including at least the magnetic coupling element, from the C value of the capacitor configuring the resonance circuit, the resonance frequency of the resonance circuit and the Q value of the magnetic coupling element (resonance circuit).

The control circuit 33 is a circuit for controlling the foreign substance detection circuit 32 and for determining presence or absence of a foreign substance metal between (in the gap) the power transmission unit 12 and the power reception unit 22 based on the measurement result using the foreign substance detection circuit 32, and is also a circuit for transmitting the determination result to the control circuit 26 of the power reception device 21. For example, the control circuit 33 compares the R value of the resonance circuit which is calculated based on the measured Q value with a threshold value which is stored in a memory (not illustrated) in advance and determines that the foreign substance metal is present in the vicinity of the detection coil in a case where the R value and the threshold value have a predetermined relationship.

Further, the power transmission unit 12 used in the present embodiment has at least one (here, one) of the power transmission coil L1, and the power reception unit 22 has at least one (here, one) of the power reception coil L2. These power transmission coils L1 and L2 can be magnetically coupled with each other. In addition to the power transmission coil L1 and the power reception coil L2, the power transmission unit 12 and the power reception unit 22 may have one or a plurality of LC resonance device which are configured to have one or a plurality of coils, or the coil and the capacitor.

These coils (power transmission coil L1, power reception coil L2 and the like) are not limited to an open coil (conductive coil) having a shape where a conductive wire (material) is wound in a plurality of turns. For example, it may be an open loop (conductive loop) having a shape where the conductive wire is wound in one turn. In addition, as the conductive coil or the conductive loop, a coil (wounded coil) or a loop (wounded loop) where the conductive wire is wound, and a coil (pattern coil) or a loop (pattern loop) which is configured to have a conductive pattern on a printed board (printed wiring board) or a flexible printed board (flexible printed wiring board) or the like are used. In addition, the pattern coil and the pattern loop may be also configured to have the printed or deposited conductive material, or the processed conductive sheet metal or sheet.

Operation Example of Non-Contact Power Supply System

In the non-contact power supply system 100, the high frequency power generation circuit 13 supplies a predetermined high frequency power (AC signal) for performing the power transmission with respect to the power transmission coil L1 and the resonance capacitor C1 (LC resonance device) which are inside the power reception unit 12, in the power supply device 10. Thereby, the magnetic field (magnetic flux) is generated in the power transmission coil L1 inside the power reception unit 12. At this time, if the electronic device 20A as a power supply target (charging target) is placed on (or moved close to) the upper surface (power supply surface S1) of the power supply device 10, the power transmission coil L1 inside the power supply device 10 and the power reception coil L2 inside the electronic device 20A are moved close to each other in the vicinity of the power supply surface S1.

In this manner, if the power reception coil L2 is disposed close to the power transmission coil L1 generating the magnetic field (magnetic flux), the power reception coil L2 is induced by the magnetic flux generated from the power transmission coil L1 to generate an electromotive force in the power reception coil L2. In other words, the magnetic field is generated crosslinking to each of the power transmission coil L1 and the power reception coil L2 by an electromagnetic induction or a magnetic field resonance. Thus, the power is transmitted (non-contact power supply P1 in FIG. 3) from the power transmission coil L1 (primary side, the power supply device 10 side, power transmission unit 12 side) to the power reception coil L2 (secondary side, electronic device 20A side, power reception unit 22 side). At this time, in the power supply device 10 side, the resonance operation (resonance frequency f1) is performed using the power transmission coil L1 and the resonance capacitor C1, and in the electronic device 20A side, the resonance operation (resonance frequency f2≈f1) is performed using the power reception coil L2 and the resonance capacitor C2.

Then, in the electronic device 20A, the AC power acquired from the power reception coil L2 is supplied to the rectifying circuit 24 and the voltage stabilizing circuit 25 to perform the charging operation as follows. That is, the AC power is converted to a predetermined DC power by the rectifying circuit 24 and thereafter, based on the rectified DC power, the voltage stabilization operation is performed by the voltage stabilizing circuit 25 and then, the battery 28 or a battery (not illustrated) inside the load 27 is charged. In this way, in the electronic device 20A, the charging operation is performed based on the power acquired from the power reception unit 22.

That is, in the present embodiment, when the electronic device 20A is charged, for example, a terminal connection to an AC adaptor and the like is not necessary and the charging may be easily started (non-contact power supply is performed) by only placing the device on (moving close to) the power supply surface S1 of the power supply device 10. This leads to a reduced burden on the user.

On the other hand, in the foreign substance detection device 31 of the electronic device 20A, the Q value measurement and the R value calculation of the LC resonance device configured to have the detection coil L3, or the detection coil L3 and the resonance capacitor C3 are performed using the AC signal of the different frequencies (f3; f3≠f1, f3≠f2) from the frequencies (f1, f2) of the AC signal flowing into the power transmission coil L1 and power reception coil L2. In addition, the foreign substance detection device 31 can determine presence or absence of a foreign substance metal between the power transmission unit 12 and the power reception unit 22 based on the change in the R value.

Then, the determination on the result, the presence or absence of the foreign substance metal using the foreign substance detection device 31 is transmitted from the power reception device 21 inside electronic device 20A to the power transmission device 11 inside the power supply device 10 by a communication means such as the load modulation.

Further, in a case where the foreign substance detection device 31 detects that the foreign substance metal is present (in the gap) between the power transmission unit 12 and the power reception unit 22, the control for limiting or stopping the power transmission is performed by the control circuit 16 inside the power transmission device 11 or the control circuit 26 inside the power reception device 21. As a result, the heat generation or ignition due to the foreign substance metal, or malfunctions of or damages to the non-contact power supply system may be prevented in advance.

5. Measurement Data (1) (Case of Detection Coil L3)

A change in the electric characteristics (Q value, R value) of the detection coil due to presence or absence of a foreign substance metal is measured. Herein, the measurement result will be described.

FIGS. 5A and 5B respectively illustrate one example of the measurement result related to the change in the electric characteristics (Q value, R value) of the detection coil L3 due to presence or absence of a foreign substance metal, in a case where the foreign substance metal detection is performed using the magnetic coupling element (detection coil L3) which is different from the power transmission coil L1 and the power reception coil L2. FIG. 5A is an example of a case where the above-described electric characteristic is the Q value, and FIG. 5B is an example of a case where the above-described electric characteristic is the R value.

In addition, FIGS. 5A and 5B are to compare cases where the distances between the detection coil L3 and the foreign substance metal are changed. Furthermore, the comparing is also performed among electric characteristics (illustrated in dashed line) of the detection coil L3 in a case of only the secondary side device, electric characteristics (illustrated in circle and solid line) of the detection coil L3 in a case where the secondary side device is disposed on the primary side device, and electric characteristics (illustrated in triangles and dashed line) of the detection coil L3 in a case where the foreign substance metal is disposed between the secondary side device and the primary side device. Each horizontal axis represents the distance (mm) between the detection coil L3 and the foreign substance metal, and each vertical axis represents the change (%) in the Q value of the detection coil L3.

The distance between the detection coil L3 and the foreign substance metal (a foreign substance metal 43) as illustrated in FIG. 6 is adjusted by changing a distance Y along the y axis direction between the detection coil L3 and a housing of the secondary side device. In addition, in FIGS. 5A and 5B, "Min." and "Max." respectively indicate the minimum value and maximum value of the measurement value obtained by changing a arrangement position of the foreign substance metal with respect to the power reception coil L2 in the x axis direction within a predetermined range.

As illustrated in FIGS. 5A and 5B, if the electric characteristics (Q value, R value) of the detection coil L3 are 100% in a case of only the secondary side device, in a case where the secondary side device is disposed on the primary side device, the R value of the detection coil L3 is increased (worsened) equal to or more than 100% and the Q value of the detection coil L3 is decreased (worsened) equal to or less than 100%. This is because the detection coil L3 is subjected to the influence due to the metal or magnetic material, magnet and the like which are arranged inside or in the vicinity of the primary side device.

In a case where the foreign substance metal is disposed between the secondary side device and the primary side device, the R value of the detection coil L3 is further increased (worsened) and the Q value of the detection coil L3 is further decreased (worsened). This is because the detection coil L3 is also subjected to the influence due to the foreign substance metal which is disposed between the secondary side device and the primary side device, in addition to a metal or a magnetic material, a magnet and the like which are disposed inside or in the vicinity of the primary side device.

On the other hand, it is appreciated that a difference between the electric characteristic of the detection coil L3 in a case where the secondary side device is disposed on the primary side device and the electric characteristic of the detection coil L3 in a case where the foreign substance metal is disposed between the secondary side device and the primary side device is larger in the R value rather than the Q value. The larger this difference is, the higher the foreign substance metal detection accuracy is. However, the reason why the R value is larger than the Q value is as described in the above "R value measurement principle".

In addition, it is appreciated that as the distance between the detection coil L3 and the foreign substance metal is close, the difference of the R value is larger than the Q value. This is because if a distance between the detection coil L3 and the foreign substance metal becomes close, a distance between the detection coil L3 and the metal or the magnetic material, magnet and the like which are disposed inside or in the vicinity of the primary side device also becomes close. That is, since the detection coil L3 is easily subjected to the influence due to the metal or the magnetic material, the magnet and the like which are disposed inside or in the vicinity of the primary side device, the L value of the detection coil L3 varies significantly, and the Q value of the detection coil L3 is unlikely to vary due to the presence or absence of a foreign substance metal.

As described also in the above "R value measurement principle", in a case of a configuration where the L value of the detection coil L3 varies significantly, focusing on the R value rather than the Q value enhances a detection accuracy of the foreign substance metal is high.

6. Measurement Data (2) (Case of Power Reception Coil L2)

The change in the Q value of the power reception coil due to presence or absence of a foreign substance metal was measured. Hereinafter, the measurement result will be described.

Figure 7A:
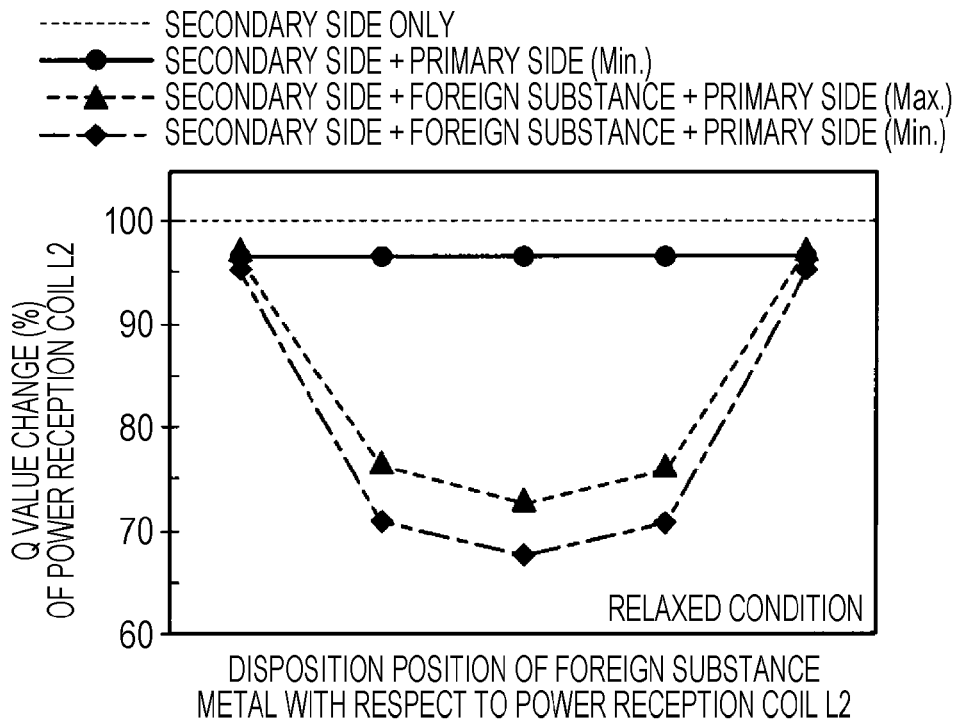
FIGS. 7A and 7B are views illustrating one example of the measurement result related to a change in the Q value of a power reception coil due to presence or absence of a foreign substance metal.
Figure 7B:
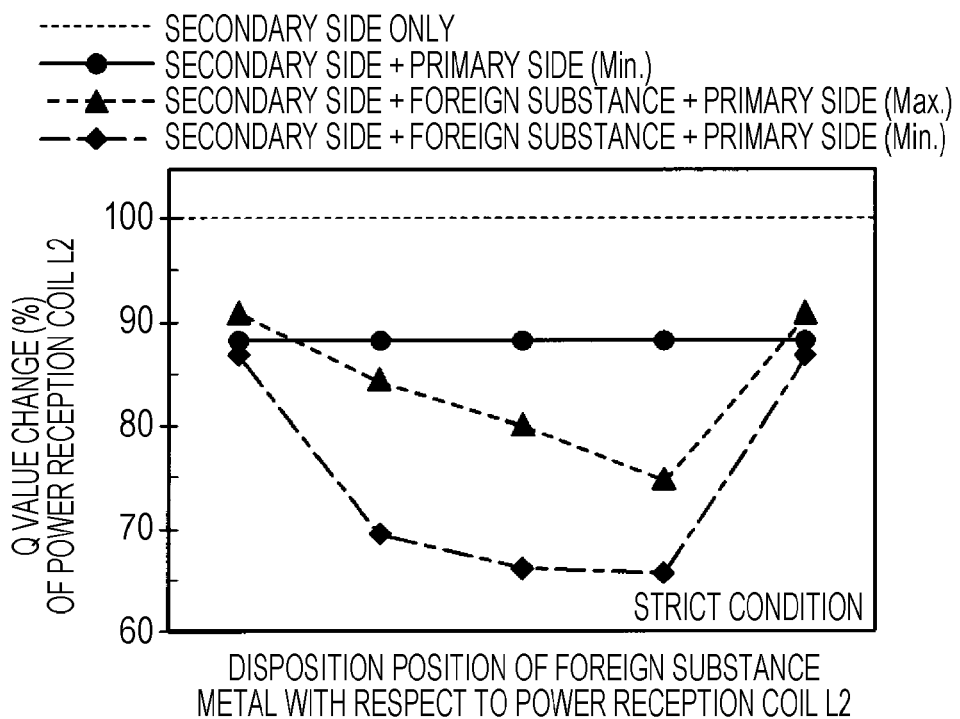

FIGS. 7A and 7B respectively illustrate one example of the measurement result related to the change in the Q value of the power reception coil L2 due to presence or absence of a foreign substance metal in a case where the foreign substance detection is performed using the power reception coil L2. That is, one example of the case is illustrated where the power reception coil L2 and the detection coil L3 are used.

However, in this case, it is necessary to add a foreign substance detection function (foreign substance detection device 31) such as a foreign substance detection circuit 32 and a control circuit 33 inside the power reception device 21. In addition, in this case, the foreign substance detection device 31 may be provided or may not be provided in addition to the power reception device 21 performing the non-contact power supply or the foreign substance detection.

Here, FIG. 7A illustrates one example of a case (relaxed measurement condition) where the metal and the magnetic material which have a small size are used inside the primary side device, and FIG. 7B illustrates one example of a case (strict measurement condition) where the metal, the magnetic material and the magnet which have a large size are used inside the primary side device.

In addition, in FIGS. 7A and 7B, cases are compared where the arrangement position of the foreign substance metal is changed with respect to the power reception coil L2. Furthermore, comparing are also performed among electric characteristics (illustrated in dashed lines) of the power reception coil L2 in a case of only the secondary side device (electronic device), electric characteristics (illustrated in circles and solid lines) of the power reception coil L2 in a case where the secondary side device is disposed on the primary side device, and the maximum value (illustrated in triangles and dashed lines) and the minimum value (illustrated in diamonds and chain lines) of electric characteristics of the power reception coil L2 in a case where the foreign substance metal is disposed between the secondary side device and the primary side device. The horizontal axis represents the arrangement position of the foreign substance metal with respect to the power reception coil L2, and the vertical axis represents the change (%) in the Q value of the power reception coil L2. Here, the arrangement position of the foreign substance metal with respect to the power reception coil L2 is shifted several mm to several cm in order.

As illustrated in FIG. 8, the arrangement position of the foreign substance metal (foreign substance metal 43) with respect to the power reception coil L2 was adjusted by changing the distance X along the x axis direction between a predetermined position (for example, the center in the x axis direction or the center of gravity) of the power reception coil L2 and the foreign substance metal 43.

As illustrated in FIGS. 7A and 7B, it is appreciated that compared to the Q value of the power reception coil L2 in a case of only the secondary side device, the Q value of the power reception coil L2 decreases when the secondary side device is disposed on the primary side device, and the Q value of the power reception coil L2 when the foreign substance metal is disposed between the secondary side device and the primary side device further decrease.

In addition, it is appreciated that change amount (decreased amount) is the Q value, illustrated in a solid line, of the power reception coil L2 when the secondary side device is disposed on the primary side device remarkably varies between a case (relaxed measurement conditions) where the metal, and magnetic material and the magnet which have a small size are used inside the primary side device, and a case (strict measurement conditions) where the metal, magnetic material and the magnet which have a large size are used inside the primary side device. For example, the foreign substance detection device 31 is provided inside a certain secondary side device, in this case, it is very difficult to set the reference value (threshold value) of the Q value used in determining the presence or absence of a foreign substance metal, a plurality of types of the primary side devices capable of performing the non-contact power supply with respect to the secondary side device exist, and the metal, magnetic material and the like which are provided inside or in the vicinity of the a plurality of types of the primary side devices remarkably vary.

In addition, in a case where a non-contact power supply and foreign substance metal detection system is constructed to correspond to the plurality of types of the primary side devices, it is necessary to indulgently set the reference value (threshold value) of the Q value. Therefore, there is a high possibility that the detection accuracy of the foreign substance metal may be significantly degraded.

In addition, in the primary side devices which are not the objects when setting the reference value (threshold value) of the Q value or a new type of a primary side devices to be provided in the future. Therefore, since compatibility is not expected, there is a possibility that the non-contact power supply and foreign substance detection system itself may be failed.

Next, the change in the R value of the power reception coil due to presence or absence of a foreign substance metal was measured. Hereinafter, the measurement result will be described.

FIGS. 9A and 9B respectively illustrate one example of the measurement result related to the change in the R value of the power reception coil L2 due to presence or absence of a foreign substance metal in a case where the foreign substance detection is performed using the power reception coil L2.

Here, FIG. 9A illustrates one example of a case (relaxed measurement condition) where a small size of the metal and magnetic material is used inside the primary side device, and FIG. 9B illustrates one example of a case (strict measurement condition) where a large size of the metal, magnetic material and magnet is used inside the primary side device.

As illustrated in FIGS. 9A and 9B, it is appreciated that compared to the R value of the power reception coil L2 in a case of only the secondary side device, the R value of the power reception coil L2 decreases when the secondary side device is disposed on the primary side device, and the R value of the power reception coil L2 when the foreign substance metal is disposed between the secondary side device and the primary side device remarkably increases.

In addition, it is appreciated that the change amount (decreased amount) in the R value, illustrated in the solid line, of the power reception coil L2 when the secondary side device is disposed on the primary side device remarkably varies between a case (relaxed measurement condition) where the metal and magnetic material which have a small size are used inside the primary side device, and a case (strict measurement condition) where the metal, magnetic material and magnet which have a large size are used inside the primary side device. In this manner, in the case where the foreign substance detection system which focuses on the change amount in the R value is formed, it is recognized that the reference value (threshold value) of the R value to be used to determine presence or absence of a foreign substance metal is easily set. For example, in a case (in a state where the foreign substance capable of generating heat due to the magnetic flux is not present at its surrounding) of only the secondary side device, it is very easy and sufficient if the R value of the power reception coil L2 (or resonance circuit) is set as a reference value (threshold value) which is necessary for determining the presence or absence of a foreign substance metal.

As described above, in the foreign substance detection system which focuses on the change amount in the R value, advantages may be obtained in which the detection accuracy of the foreign substance metal is higher, setting of the reference value (threshold value) of the R value to be used to determine presence or absence of a foreign substance metal is easier, compared to the foreign substance detection system which focuses on the change amount in the Q value.

In addition, in the above-described "Measurement Data (2)", the case where the foreign substance detection is performed using the power reception coil L2 has been described, but the case where the foreign substance detection is performed using the power transmission coil L1 may be also assumed.

7. Modification Example

In general, in the non-contact power supply system, in order to increase the detection accuracy of the foreign substance metal, the power supply from the power supply device is frequently stopped during the foreign substance detection process. During that time, the power is not supplied from the power supply device and therefore in a case where the foreign substance detection device is provided in the electronic device of the power reception side, a large scaled battery is provided to activate a circuit for measuring the Q value of the resonance circuit. However, inconveniently, the large scaled battery may exert an adverse effect on the product life of the electronic device, may make it difficult to miniaturize the electronic device, or may cause the foreign substance detection not to be performed since the power charge is not performed immediately when the battery capacity is emptied. In the modification example, battery-less electronic devices (power reception device) having no large scaled battery will be described.

Figure 10:
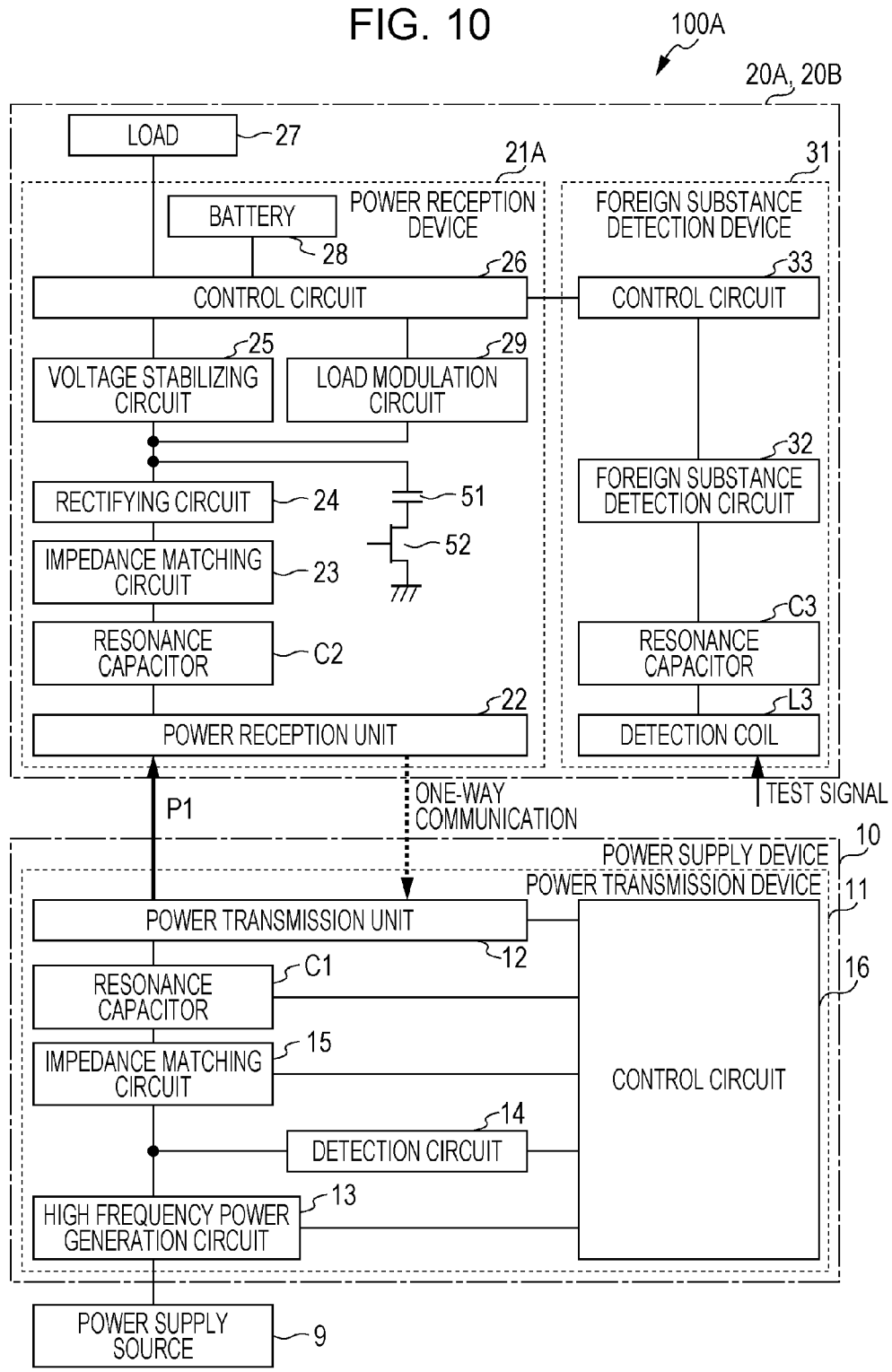
FIG. 10 is a block diagram illustrating a modification example of the non-contact power supply system according to another embodiment of the present disclosure.

FIG. 10 is a block diagram illustrating a modification example of the non-contact power supply system according to one embodiment of the present disclosure.

The non-contact power supply system 100A illustrated in FIG. 10 is different from the non-contact power supply system 100 described above in that a capacitor 51 (an example of power charging unit) and a switch 52 (an example of switching unit) are provided for the power reception device 21A. In the example illustrated in FIG. 10, the one end of the capacitor 51 is connected to a connection middle point between the rectifying circuit 24 and the voltage stabilizing circuit 25 and the other end is grounded via a switch 52. In addition, the power reception device 21A is provided with the battery 28, but may be not provided with the battery 28 since the capacitor 51 provided.

For example, when the power supply is started from the power supply device 10, the switch 52 is turned "on" and turned "off" after "on" during a predetermined time period even after the power supply is stopped. The on/off operation of the switch 52, for example, is controlled by the control circuit 26. By the operation of the switch 52, the resonance capacitor 51 is charged after the start of the power supply and after the stop of the power supply, the foreign substance detection process of the foreign substance detection device 31 is performed using the power discharged from the capacitor 51. For example, switching elements such as a transistor, a MOSFET or the like are adopted to the switch 52. In the present embodiment, the MOSFET is used.

Figure 11:
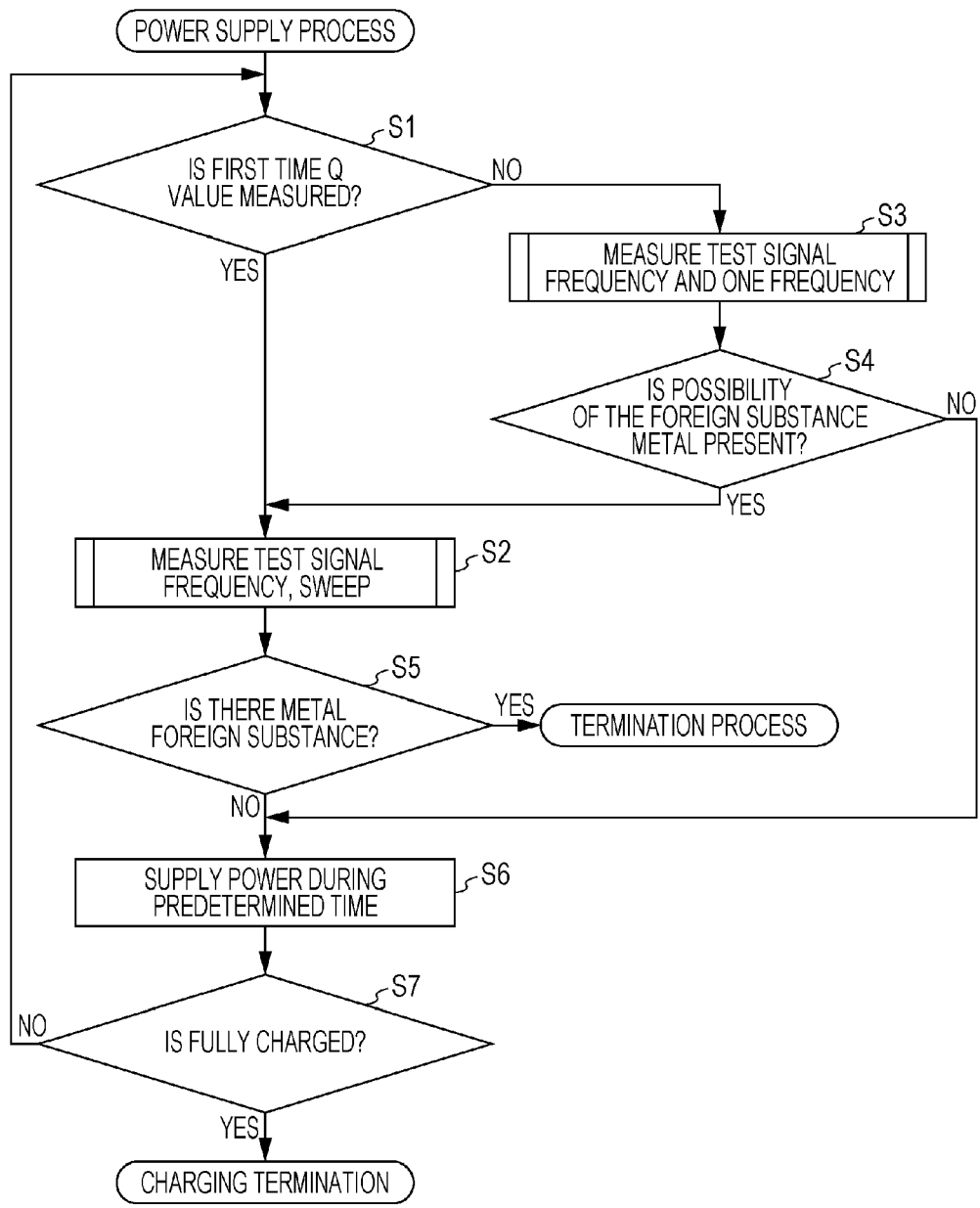
FIG. 11 is a flow chart illustrating one example of a process when supplying a power in the non-contact power supply system.

FIG. 11 is a flow chart illustrating a process when supplying the power of the non-contact power supply system 100A.

First, if the power supply device 10 (primary side) is activated and the electronic device 20A (secondary side) is placed close to the power supply device 10, a negotiation is performed between the power supply device 10 and the electronic device 20A. The power supply is started after the power supply device 10 and the electronic device 20A recognize each other. The foreign substance detection device 31 of the electronic device 20A performs the measurement of the Q value and the calculation of the R value when starting the power supply, but determines whether or not the number of the Q value measurements is the first time (step S1).

As one example, if it is immediately after the power of the power supply device 10 or the electronic device 20A is turned on, each device determines that it is the first measurement of the Q value. Alternately, as a result on the negotiation, the power supply device 10 determines that the Q value measurement is first time, based on the ID information (identification information) of the electronic device 20A when the electronic device 20A is the first communication partner. Alternatively, the power supply device 10 may grasp the number of the Q value measurements at the time of negotiating by receiving the result on the Q value measurement number calculated by and supplied from the electronic device 20A.

In addition, as another example, the first Q value measurement may be determined by an elapsed time period from the previous time of the Q value measurement. The power supply device 10 (and the electronic device 20A) has a clock unit (not illustrated), and, when the measurement was performed the measured value is stored in the memory (not illustrated) in association with the measurement time. Then, if it is a time difference exceeding a predetermined value, it is determined to be the first time of the Q value measurement by comparing the previous time of the Q value measurement time and the current Q value measurement time. The Q value measurement number is calculated based on the reference where the Q value measurement causing, for example, a frequency sweep is the first time. In addition, a timer function of the clock unit may be started during the previous time the Q value measurement, and the first Q value measurement may be also determined based on the lapsed time of the timer.

Then, in a case where it is determined to be the first time of the Q value measurement, the foreign substance detection device 31 of the electronic device 20A obtains the largest Q value among a plurality of the obtained Q values of the resonance circuit which are obtained using a plurality of frequencies (sweep measurement) in a test signal (sine wave) for measuring, which is generated inside (step S2). The frequency of the test signal is stored in the memory when the Q value is the largest.

In order to measure the Q value, it is necessary to input the sine wave having the resonance frequency of the resonance circuit to the resonance circuit of the electronic device 20A. However, the resonance frequency is changed due to variations in the component quality of the electronic device 20A, variations in the positional relationship between the coil and the metal inside the device (for example, the housing) when providing the coil in the housing, environments around the detection coil L3, or the mixture of the foreign substance metal and the like. Therefore, considering the variations of the resonance frequency, it is preferable to detect the resonance frequency by measuring (frequency sweep) and using the plurality of different frequencies in an appropriate range (measurement range) to some extent.

With regard to the frequency sweep, when considering the whole non-contact power supply system 100A, the first time of the Q value measurement is necessary, but the frequency sweep may be omitted from the second time measurement. As an example in which the frequency sweep can be omitted in the Q value measurement after the second time, there is a case where the positional relationship between the power supply device 10 and the electronic device 20A does not significantly vary when compared to the first time Q value measurement.

On the other hand, in the determination process of the Step S1, if the Q value measurement is not the first time, the foreign substance detection device 31 of the electronic device 20A obtains the Q value using the test signal of the frequency obtained in the first time Q value measurement (step S3).

The foreign substance detection device 31 of the electronic device 20A determines whether or not there is a possibility that the foreign substance metal may be present (step S4). If there is no possibility that the foreign substance metal may be present, the process proceeds to step S6.

On the other hand, in the determination process of the step S4, if there is a possibility that the foreign substance metal may be present, the process proceeds to the step S2, and the foreign substance detection device 31 of the electronic device 20A performs the frequency sweep of the test signal and obtains the largest Q value among the a plurality of Q values.

After the process of the step S2 is completed, the foreign substance detection device 31 of the electronic device 20A determines presence or absence of a foreign substance metal based on the Q value obtained by the calculation (step S5). If the foreign substance metal is present, the power supply is compulsively completed or a warning is given to the user as a termination process. As the compulsory process of the power supply, there is a method where the power supply device 10 stops the power supply or the electronic device 20A stops receiving the power even though the power supply device 10 performs the power transmission.

In the above-described steps S2 to S5, the Q value measurement is performed using the power charged in the power storage unit (capacitor 35). For example, in a case of the frequency sweep, after charging electric charges enough to measure the Q value (that is, voltages V1 and V2) into the capacitor 35 with regard to the test signal of one frequency, the Q value measurement is performed, recharging is performed, and then the Q value measurement is repeated with regard to the test signal of the next frequency.

Then, in the step S5, if there is no foreign substance metal, the power supply is performed from the power supply device 10 to the electronic device 20A during a predetermined time period (step S6).

Finally, the electronic device 20A determines whether or not the battery (not illustrated) has been fully charged and communicates the result with the power supply device 10 (step S7). If fully charged, the charging process is completed, and if not fully charged, the process returns to the step S1 and the above process is repeated. In addition, the determination on whether or not full charged and the communication may be performed during the power supply.

In this way, only the first time Q value measurement is performed using the frequency sweep and the following Q value measurement from the second time may be performed using only the test signal of the frequency optimized in the first time. However, if determined that there is a possibility that the foreign substance metal may be present, since there is a possibility of the frequency deviation due to the changed positional relationship between the power reception coil L2 and the secondary side coil. Accordingly, the determination is performed by sweeping the frequency again. Even though the frequency is swept, if determined that the foreign substance metal is present, the power supply is compulsively completed or the warning is given to the user. This method enables the Q value measurement time to be significantly decreased.

If the consumption current of the foreign substance detection device 31 is small to some extent and the time for the Q value measurement and R value calculation is short, the Q value can be measured during the time when stopping the power supply from the power supply device 10. In addition, when stopping (when measuring the Q value) the magnetic field (magnetic flux) outputting from the power supply device 10, it is desirable that the load 27 is electrically and reliably disconnected from the power reception device 21A. For example, a switch is provided between the device and the loads 27 to be turned off when the magnetic field (magnetic flux) is supplied to the power reception device 21A. When the power charge to the capacitor 51 other than the device is performed or when the communication with the outside is performed, the load may be disconnected from the power reception device 21.

When measuring the Q value, the foreign substance detection device 31 supplies the test signal to the resonance circuit configured to have the detection coil L3 and the resonance capacitor C3, in the timing when the power supply is stopped, and measures the Q value of the resonance circuit using the two voltage waves (voltages V1 and V2) detected in one end and the other end of the resonance capacitor C3. The R value is obtained from the measured Q value, and the foreign substance metal detection is performed by comparing the obtained R value and the preset threshold value.

Whenever measuring the Q value, the power reception device 21A of the present embodiment charges the capacitor 51 and uses the power to drive the foreign substance detection device 31. Thereby, if the power supply is not performed from the primary side to the secondary side, the power reception device 21A may perform the Q value measurement and the R value calculation even without using the secondary side battery. Therefore, it is not necessary to provide the large scaled battery for detecting the foreign substance metal in the secondary side or the complicate circuit for controlling the power, whereby enabling miniaturizing, lightening or cost saving for the electronic device such as a portable device.

8. Others

In the embodiment described above, a case has been described where the foreign substance detection device including the detection coil is disposed inside the electronic device as the secondary side device (power supply target device). However, the present disclosure is not limited thereto, and the foreign substance detection device including the detection coil may be disposed inside the power supply device as the primary side device. In such a case, it may be considered that the predetermined coil described in the above first embodiment is replaced by the power transmission coil, and the power transmission coil is replaced by the power reception coil. In addition, the foreign substance detection device including the detection coil may be disposed inside both of the primary side device and the secondary side device.

Thus, the foreign substance detection device including the detection coil may be disposed inside the other device which is a separate body from the primary side device and the secondary side device. That is, the foreign substance detection device including the detection coil described in the above embodiment may be disposed inside at least any one of the primary side device, the secondary side device as the power supply target device, and the other device which is a separate body from the primary side device and the secondary side device.

In addition, in the above each embodiment, only a case has been described where the power transmission coil and the power reception coil are disposed one by one, but is not limited to such a case. For example, the power transmission coil and the power reception coil may be disposed in multiple (two or more).

Furthermore, in addition to the above-described LC resonance device (resonance circuit), the other LC resonance device (resonance circuit) may be used in the non-contact power supply system (non-contact power supply function or the foreign substance detection function).

In addition, in the above each embodiment, a spiral shaped (plane shaped) coil or a helical shaped coil where windings are wound in the thickness direction may be adopted to each coil (power transmission coil, power reception coil, detection coil), but the embodiment is not limited to the example. For example, each coil may be configured to have an alpha winding shape where the spiral shaped coil is disposed to be folded in two layers or further more layers.

In addition, the power transmission coil or the power reception coil may be configured to have a figure eight shape, a chessboard shape, or a lattice shape, which is capable of reducing the magnetic flux leakage.

In addition, the detection coil is integrated with the power transmission coil, the power reception coil or the like and thereby the non-contact power supply coil such as the power transmission coil or the power reception coil may be shared as the detection coil. Further, the coil used for a use other than the non-contact power supply such as an induction heat coil or a radio communication coil may be shared as the detection coil.

That is, in the above each embodiment, an example of the case has been described where the magnetic coupling element is used as the detection coil, but the embodiment is not limited thereto. For example, there may be a case where the magnetic coupling element is the non-contact power supply coils (power transmission coil, power reception coil), the induction heat coil, the radio communication coil and the like and these coils are used to function as the foreign substance detection.

In addition, the magnetic material, the metal material or the like may be disposed inside the power supply unit of the power transmission device, inside the power reception unit of the power reception device, and in the vicinity of the detection coil, so as to prevent the unnecessary magnetic flux (magnetic force line, magnetic field) from being leaked, or so as to improve the transmission efficiency (power supply efficiency) or the like.

In addition, as each resonance capacitor (particularly, resonance capacitor inside the foreign substance detection device), without being limited to the case where the fixed electrostatic capacitance value is used, a configuration (for example, a configuration to switch a connection paths among a plurality of capacitance elements using the switch and the like) may be used which enables the electrostatic capacitance value to be varied. In such a configuration, the resonance frequency can be controlled (optimized) by adjusting the electrostatic capacitance value.

Furthermore, in each embodiment described above, the respective configuring elements such as the power supply device and the electronic device has been described specifically, but it is not necessary to include all the component elements, and another configuring element may be further included. For example, a communication function, a detection function, a control function, a display function, an secondary device authentication function, a function determining whether or not the secondary side device is present on the primary side device, a function detecting the mixed foreign substance metal using a separate means from the present disclosure may be provided inside the power supply device (power transmission device) or the electronic device (power reception device).

In addition, in the above each embodiment described above, a case has been described where the load modulation is used as the communication function as an example, but the embodiment is not limited to the case. For example, the modulation method in addition to the load modulation may be used as the communication function, and the communication may be performed by providing an antenna for the radio communication or the coil for radio communication, and using the other method in addition to the modulation method. On the other hand, the communication function itself may not be provided depending on the configuration of the non-contact power supply function (power transmission device and power reception device) and the foreign substance detection function (foreign detection device). Similarly, various component elements (sites, components, circuits and the like) used in each embodiment described above may not provide some of them depending on the configuration of the non-contact power supply function (power transmission device and power reception device) and the foreign substance detection function (foreign detection device).

In addition, in the above each embodiment described above, a case has been described where a plurality (two) of the electronic devices are provided inside the non-contact power supply system as an example, but the embodiment is not limited to the example, and one, three or more electronic devices may be provided inside the non-contact power supply system.

In addition, in the above each embodiment described above, as an example of the power supply device, the charging tray for a small electronic device (CE device) such as a portable phone has been described, but the power supply device is not limited to such a household charging tray and may be applied as the power charging device of the various electronic device. Further, the power supply device may not necessarily have such a tray type and for example, may be a stand for the electronic device such as a so called cradle and the like.

In addition, in the above each embodiment, the electronic device has been described as an example of the power supply target device, but without being limited thereto, the power supply target device (for example, vehicles such as electric vehicles) may be used in addition to the electronic device. For example, in a case where the power supply target device is used as the electric vehicle, it may be possible to detect the foreign substance metal which is present between the detection coil and the power supply device which are provided in the electric vehicle, being mixed in mud and attached to the vehicle body.

In addition, the present disclosure may adopt the following configurations.

(1) A detection device including: one or the plurality of magnetic coupling elements configured to have one or the plurality of coils; and a detection unit that measures or calculates an effective resistance value of the magnetic coupling element or an effective resistance value of a circuit including at least the magnetic coupling element and determines a presence or absence of a foreign substance based on a change in the effective resistance value.

(2) The detection device according to the above-described (1), wherein the circuit including at least the magnetic coupling element is a resonance circuit.

(3) The detection device according to the above-described (2), wherein the effective resistance value is at least an effective resistance value in the vicinity of a resonance frequency of the resonance circuit.

(4) The detection device according to the above-described (3), wherein the effective resistance value is measured or calculated using at least a measurement result or a calculation result on at least any one of a Q value of the resonance circuit and the resonance frequency of the resonance circuit.

(5) The detection device according to the above-described (3) or (4), wherein in a state where the foreign substance is not around the one or the plurality of magnetic coupling elements, the effective resistance value of the magnetic coupling element or the effective resistance value of the resonance circuit including at least the magnetic coupling element is set to a threshold value used for determining presence or absence of a foreign substance.

(6) The detection device according to the above-described (4) or (6), wherein at least any one of the Q value and the resonance frequency is measured or calculated using at least the measurement result or calculation result on a voltage amplitude of a high frequency power flowing in the magnetic coupling element or the resonance circuit.

(7) The detection device according to the above-described (6), wherein the effective resistance value is measured or calculated using at least the measurement result or the calculation result on the Q value of the resonance circuit and the resonance frequency of the resonance circuit.

(8) The detection device according to the above-described (1), wherein the effective resistance value is measured or calculated using at least a measurement result or a calculation result on a voltage amplitude of a high frequency power flowing in the magnetic coupling element or power flowing in the circuit including at least the magnetic coupling element.

(9) The detection device according to the above-described (8), wherein the effective resistance value is measured or calculated using at least at least two or more measurement results or calculation results among a voltage amplitude, a voltage phase, a current amplitude and a current phase of the high frequency power flowing in the magnetic coupling element or the high frequency power flowing in the circuit including at least the magnetic coupling element.

(10) The detection device according to the above-described (1), wherein the magnetic coupling element is at least any one of a power reception coil used for a non-contact power supply from the power supply source, a power transmission coil used for the non-contact power supply from the power supply source, and a coil which is different from the power reception coil and the power transmission coil.

(11) The detection device according to the above-described (10), wherein the magnetic coupling element is at least any one of the power reception coil used for a non-contact power supply from the power supply source and a power transmission coil used for the non-contact power supply from the power supply source.

(12) A power reception device including: a power reception coil used for a non-contact power supply from the power supply source; one or a plurality of magnetic coupling elements configured to have one or a plurality of coils; and a detection unit that measures or calculates an effective resistance value of the magnetic coupling element or an effective resistance value of a circuit including at least the magnetic coupling element and determines a presence or absence of a foreign substance based on a change in the effective resistance value.

(13) A power transmission device including: a power reception coil used for a non-contact power supply from the power supply source; one or a plurality of magnetic coupling elements configured to have one or a plurality of coils; and a detection unit that measures or calculates an effective resistance value of the magnetic coupling element or an effective resistance value of a circuit including at least the magnetic coupling element and determines a presence or absence of a foreign substance based on a change in the effective resistance value.

(14) A non-contact power supply system configured to include a power transmission device used for a non-contact power supply to the power supply destination and a power reception device receiving a power in a non-contact manner from the power transmission device, wherein at least any one of the power transmission device and the power reception device configured includes: one or a plurality of magnetic coupling elements configured to have one or a plurality of coils; and a detection unit that measures or calculates an effective resistance value of the magnetic coupling element or an effective resistance value of a circuit including at least the magnetic coupling element and determines a presence or absence of a foreign substance based on a change in the effective resistance value.

In addition, the series of processes in the above-described each embodiment may be implemented by hardware, but may be implemented by software. In a case where the series of processes are implemented by the software, they may be implemented by a computer in which a program configuring the software is incorporated in a dedicated hardware, or a computer in which programs for carrying out various functions are installed. For example, programs configuring desired software may be installed in a general purpose personal computer.

In addition, a recording medium in which a program code of the software realizing a function of the above-described each embodiment is recorded may be supplied to a system or a device. Further, it is needless to say that the computer (or control device such as a CPU and the like) of the system or the device may obtain its functions by reading and implementing the program code stored in the recording medium.

As the recording medium for supplying the program code in this case, for example, a flexible disk, hard disk, optical disk, optical magnetic disk, CD-ROM, CD-R, magnetic tape, non-volatile memory card, ROM and the like may be used.

In addition, the functions of the above-described embodiment are obtained by implementing the program code which is read out by the computer. Further, an OS operated on the computer partially or the entirely performs based on commands of the program code. A case may be also included where the functions in the above-described embodiment are obtained using the process.

In addition, in the present specification, the process step of describing a time series process includes both of a process implementing in the time series according to the described order and a process (for example, parallel process or process depending on an object) implemented in parallel or individually.

Hitherto, the present disclosure is not limited to the above-described embodiments, and various modification examples and application examples may be of course adopted within the scope without departing from the gist of claims.

That is, since the examples of the above-described embodiment are preferred examples of the present disclosure, various technically preferable limitations are imposed thereon. However, the technical scope of the present disclosure is not limited to such embodiment as far as any intention to limit the present disclosure is not particularly included in every description. For example, the materials and amount used, processing time, process order and numerical conditions of each parameter and the like which are exemplified in the above description are only preferable examples, and a relationship between the dimension, the shape and the disposition in each of the drawings used in the description are also schematically exemplified.

The present disclosure contains the subject matter related to that disclosed in Japanese Priority Patent Application JP 2012-105768 filed in the Japan Patent Office on May 7, 2012, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A detection device, comprising:
one or a plurality of magnetic coupling elements configured to have one or a plurality of coils; and
a detection unit that measures or calculates an effective resistance value of a magnetic coupling element, of the one or the plurality of magnetic coupling elements, or of a circuit including at least the magnetic coupling element and determines a presence or absence of a foreign substance based on a change in the effective resistance value.

2. The detection device according to claim 1,
wherein the circuit including at least the magnetic coupling element is a resonance circuit.

3. The detection device according to claim 2,
wherein the effective resistance value is at least an effective resistance value in the vicinity of a resonance frequency of the resonance circuit.

4. The detection device according to claim 3,
wherein the effective resistance value is measured or calculated using at least a measurement result or a calculation result on at least any one of a Q value of the resonance circuit and the resonance frequency of the resonance circuit.

5. The detection device according to claim 4,
wherein in a state where the foreign substance is not around the one or the plurality of magnetic coupling elements, the effective resistance value of the magnetic coupling element or the effective resistance value of the resonance circuit including at least the magnetic coupling element is set to a threshold value used for determining presence or absence of the foreign substance.

6. The detection device according to claim 4,
wherein at least any one of the Q value and the resonance frequency is measured or calculated using at least the measurement result or the calculation result on a voltage amplitude of a high frequency power flowing in the magnetic coupling element or the resonance circuit.

7. The detection device according to claim 6,
wherein the effective resistance value is measured or calculated using at least the measurement result or the calculation result on the Q value of the resonance circuit and the resonance frequency of the resonance circuit.

8. The detection device according to claim 1,
wherein the effective resistance value is measured or calculated using at least a measurement result or a calculation result on a voltage amplitude of a high frequency power flowing in the magnetic coupling element or power flowing in the circuit including at least the magnetic coupling element.

9. The detection device according to claim 8,
wherein the effective resistance value is measured or calculated using at least two or more measurement results or calculation results among the voltage amplitude, a voltage phase, a current amplitude and a current phase of the high frequency power flowing in the magnetic coupling element or the power flowing in the circuit including at least the magnetic coupling element.

10. The detection device according to claim 1,
wherein the magnetic coupling element is at least any one of a power reception coil used for a non-contact power supply from the power supply source, a power transmission coil used for the non-contact power supply from a power supply source, and a coil which is different from the power reception coil and the power transmission coil.

11. The detection device according to claim 1,
wherein the magnetic coupling element is at least any one of a power reception coil used for a non-contact power supply from a power supply source and a power transmission coil used for the non-contact power supply from the power supply source.

12. A power reception device, comprising:
a power reception coil used for a non-contact power supply from the power supply source;
one or a plurality of magnetic coupling elements configured to have one or a plurality of coils; and
a detection unit that measures or calculates an effective resistance value of a magnetic coupling element, of the one or the plurality of magnetic coupling elements, or of a circuit including at least the magnetic coupling element and determines a presence or absence of a foreign substance based on a change in the effective resistance value.

13. A power transmission device, comprising:
a power transmission coil used for a non-contact power supply to the power supply destination;
one or a plurality of magnetic coupling elements configured to have one or a plurality of coils; and
a detection unit that measures or calculates an effective resistance value of a magnetic coupling element, of the one or the plurality of magnetic coupling elements, or of a circuit including at least the magnetic coupling element and determines a presence or absence of a foreign substance based on a change in the effective resistance value.

14. A non-contact power supply system configured to include a power transmission device used for a non-contact power supply to the power supply destination and a power reception device receiving a power in a non-contact manner from the power transmission device,
wherein at least any one of the power transmission device and the power reception device configured includes:
one or a plurality of magnetic coupling elements configured to have one or a plurality of coils; and
a detection unit that measures or calculates an effective resistance value of a magnetic coupling element, of the one or the plurality of magnetic coupling elements, or of a circuit including at least the magnetic coupling element and determines a presence or absence of a foreign substance based on a change in the effective resistance value.

* * * * *